US 6,544,239 B2

(12) United States Patent
Kinsey et al.

(10) Patent No.: US 6,544,239 B2
(45) Date of Patent: Apr. 8, 2003

(54) RELEASABLE LOCKING NEEDLE ASSEMBLY WITH OPTIONAL RELEASE ACCESSORY THEREFOR

(75) Inventors: P. Spencer Kinsey, Vernon, CT (US); Richard G. Holdaway, Storrs, CT (US); John M. Polidoro, Coventry, CT (US); Marius Walter Hauri, Putnam, CT (US)

(73) Assignee: Bio-Plexus Delaware, Inc., Vernon, CT (US)

( * ) Notice: Subject to any disclaimer, the term of this patent is extended or adjusted under 35 U.S.C. 154(b) by 0 days.

(21) Appl. No.: 09/734,994

(22) Filed: Dec. 12, 2000

(65) Prior Publication Data

US 2001/0018572 A1 Aug. 30, 2001

Related U.S. Application Data

(63) Continuation-in-part of application No. PCT/US99/24247, filed on Oct. 15, 1999.
(60) Provisional application No. 60/104,537, filed on Oct. 16, 1998, and provisional application No. 60/104,531, filed on Oct. 16, 1998.

(51) Int. Cl.[7] ............................................... A61M 5/32
(52) U.S. Cl. ............. 604/272; 604/164.01; 604/164.02; 604/164.06
(58) Field of Search ................................. 604/158, 161, 604/164.01, 164.06, 164.08, 167.02, 167.06, 168.01, 170.01, 170.02, 198, 263, 264, 272

(56) References Cited

U.S. PATENT DOCUMENTS

| 4,627,841 | A |   | 12/1986 | Dorr .......................... 604/158 |
| 4,828,547 | A | * | 5/1989  | Sahi et al. .................. 604/110 |
| 5,009,642 | A | * | 4/1991  | Sahi .......................... 604/110 |
| 5,120,319 | A |   | 6/1992  | Van Heugten et al. ...... 604/168 |
| 5,137,518 | A |   | 8/1992  | Mersch ....................... 604/168 |
| 5,176,655 | A |   | 1/1993  | McCormick et al. ........ 604/198 |
| 5,201,712 | A | * | 4/1993  | Bryant ..................... 604/164.02 |
| 5,250,036 | A |   | 10/1993 | Farivar ........................ 604/164 |
| 5,312,345 | A |   | 5/1994  | Cole .......................... 604/110 |
| 5,374,252 | A |   | 12/1994 | Banks et al. ................. 604/158 |
| 5,462,533 | A |   | 10/1995 | Daugherty .................. 604/164 |
| 5,472,430 | A | * | 12/1995 | Vaillancourt et al. ........ 600/576 |
| 5,476,106 | A |   | 12/1995 | Gartz ......................... 128/898 |
| 5,645,556 | A |   | 7/1997  | Yoon .......................... 606/185 |
| 5,665,102 | A |   | 9/1997  | Yoon .......................... 606/185 |
| 5,697,914 | A |   | 12/1997 | Brimhall ..................... 604/177 |
| 5,743,882 | A | * | 4/1998  | Luther .................... 604/164.05 |
| 5,817,060 | A |   | 10/1998 | Overton et al. ............. 604/164 |
| 5,951,520 | A |   | 9/1999  | Burzynski et al. .......... 604/170 |
| 6,056,726 | A |   | 5/2000  | Isaacson ..................... 604/164 |
| 6,106,499 | A |   | 8/2000  | Overton et al. ......... 604/170.01 |
| 6,391,007 | B2 |  | 5/2002  | Chang et al. ............. 604/164.1 |

FOREIGN PATENT DOCUMENTS

DE      2 147 183      4/1973
GB      802351      10/1958

* cited by examiner

*Primary Examiner*—Henry C. Yuen
*Assistant Examiner*—John Fristoe
(74) *Attorney, Agent, or Firm*—Libert & Associates; Frederick A. Spaeth

(57) ABSTRACT

A needle assembly includes a needle member (10) and a blunting member (26), the needle member (10) containing a needle cannula (12), the needle cannula (12) having a puncture tip (14) and having a needle passageway therethrough. The blunting member (26) contains a blunting probe (28) having a blunt end (28*a*). The needle cannula (12) and the blunting probe (28) are disposed telescopically one within the other without obstructing flow through the needle passageway, and are movable between a sharpened configuration in which the puncture tip (14) of the needle cannula (12) is exposed and a blunted configuration in which the blunt end (28*a*) of the blunting probe (28) extends beyond the puncture tip (14) to blunt the needle assembly. The assembly may be combined with an accessory device (such as a catheter hub, guide wire, etc.) to produce an apparatus that is lockable in a blunted configuration and that can be released by the associated accessory, or may be configured to be released by manual manipulation.

21 Claims, 16 Drawing Sheets

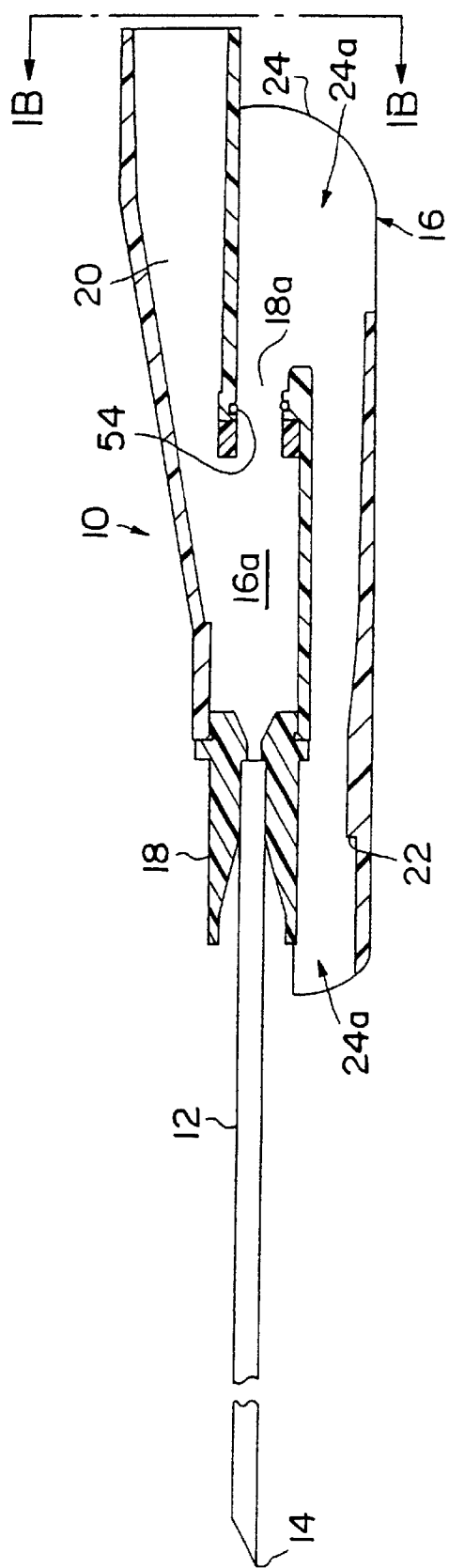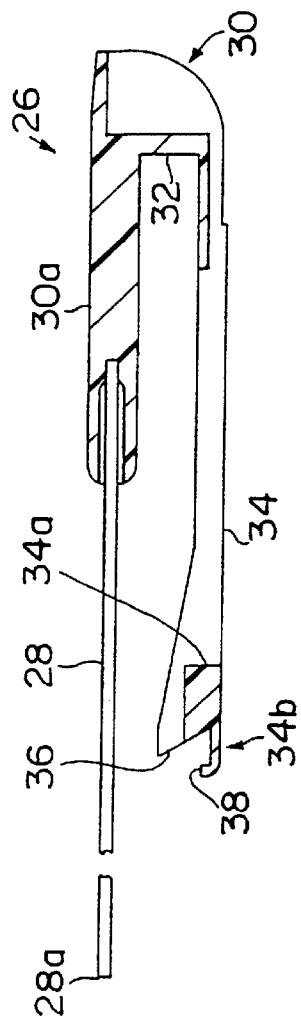

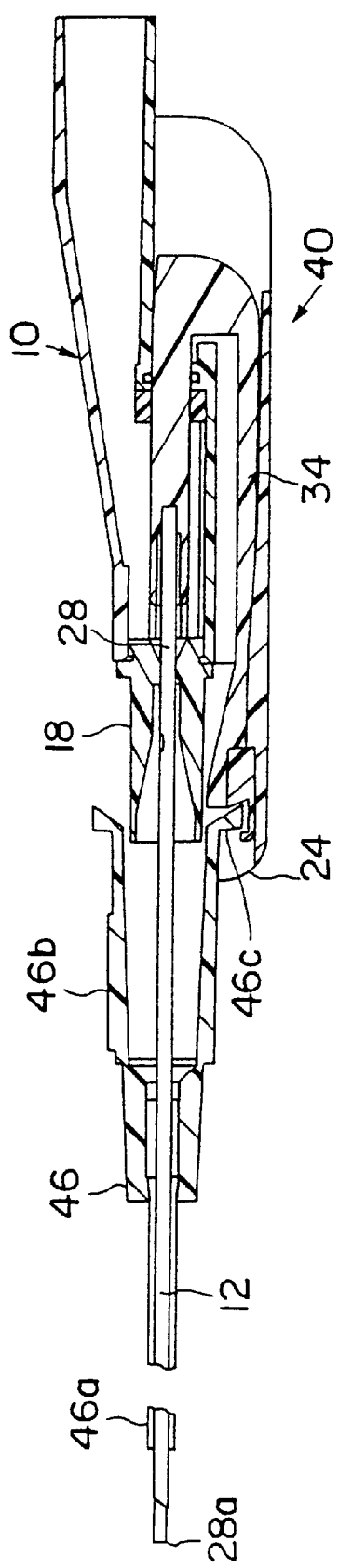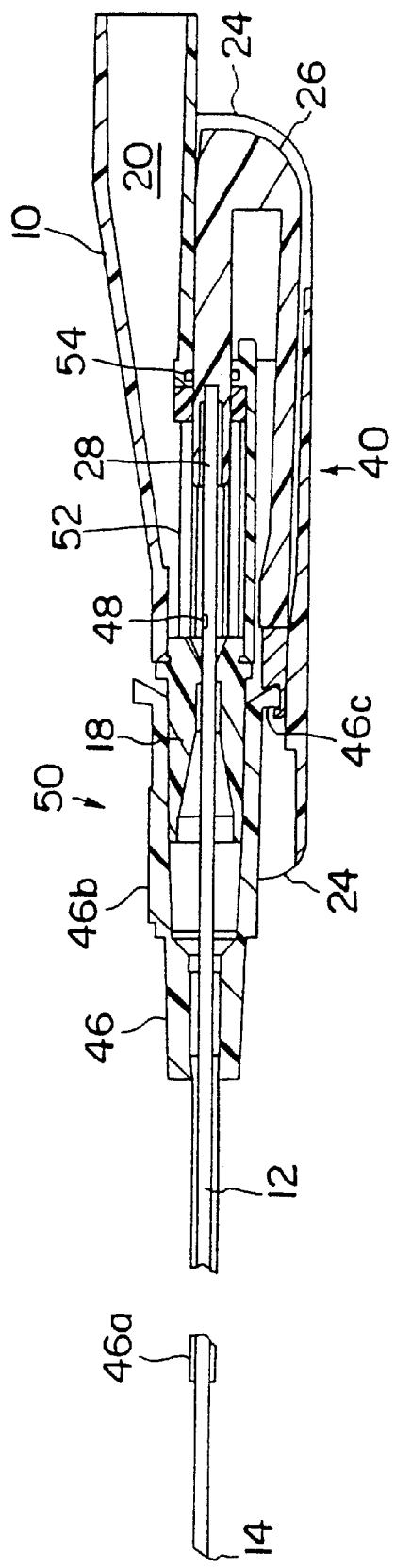
FIG. 5A
FIG. 5B

RELEASABLE LOCKING NEEDLE ASSEMBLY WITH OPTIONAL RELEASE ACCESSORY THEREFOR

CROSS REFERENCE TO RELATED APPLICATIONS

This application is a continuation-in-part of Patent Cooperation Treaty international application number PCT/US99/24247 filed date Oct. 15, 1999 which designates the U.S. and which claims the benefit of U.S. provisional application No. 60/104,537 and from U.S. provisional application No. 60/104,531, both filed on Oct. 16, 1998.

BACKGROUND OF THE INVENTION

1. Field of the Invention

The present invention pertains to self-blunting medical needles and, in particular, to needle assemblies that can lock in a blunted configuration.

2. Related Art

Many accidental needle-stick wounds are sustained by healthcare workers each day. The problem is aggravated by the trend of moving treatment out of hospitals and into doctors' offices and neighborhood clinics as part of programs to reduce healthcare costs. This trend increases the number and dispersion of healthcare workers who administer injections and draw blood samples, while reducing the frequency of such injections per individual healthcare worker. As a consequence, a larger number of less experienced people are administering injections and/or taking blood samples. Although in the past an occasional serious illness such as that caused by the hepatitis B virus was sustained as a result of an accidental needle-stick wound, the problem was not considered to be a serious one until the advent of human immunodeficiency virus (HIV) and the knowledge that this virus is transmissible to healthcare workers through needle-stick wounds from a contaminated needle. HIV causes acquired immune deficiency syndrome (AIDS), a disease, which, insofar as is presently known, is invariably fatal, and which has already killed millions and infected millions more. HIV is often referred to simply as "the AIDS virus" and the Surgeon General of the United States of America noted in a published (September, 1987) interview that there is no better way to become infected with the AIDS virus than to take blood from an AIDS patient and accidentally inflict a needle-stick wound with the contaminated needle.

This situation has stimulated activity to develop devices which reduce or eliminate the possibility of accidental needle-stick wounds without excessively increasing the unit cost of needles.

U.S. Pat. No. 5,176,655 to McCormick et al, dated Jan. 5, 1993 and entitled "DISPOSABLE MEDICAL NEEDLE AND CATHETER PLACEMENT ASSEMBLY HAVING FULL SAFETY ENCLOSURE MEANS", discloses a winged set in which a needle is movably and concentrically disposed within a tubular member to which the wings are attached. The needle is connected to the wings via straps (42). A guard device (50) is carried on the tubular member by a pair of clip legs (56). During use, the needle protrudes through the tubular member and the blocking plate bears on the side of the needle under the force of the spring. After the device has been used, the needle is withdrawn into the tubular member and the blocking plate springs down over the end of the tubular member to permanently prevent the sharp tip of the needle from exiting the tubular member (see column 3, lines 23–29, and column 6, lines 28–36). The tubular member is not adapted for engagement with any other device and no method or mechanism for re-sharpening the winged set is disclosed. Neither the needle nor the blunting member are fully enclosed one within the other.

U.S. Pat. No. 4,627,841, issued to Dorr on Dec. 9, 1986 and entitled "INFUSION NEEDLE", discloses a winged venipuncture set in which a needle is movably mounted within a catheter. A spring biases the catheter forward so that it protrudes beyond the tip of the needle and the device is configured so that when grasped for use, the catheter is withdrawn against the bias of the spring to sharpen the needle until the device is released. No locking mechanism for keeping the catheter in one position or the other is shown.

U.S. Pat. No. 5,743,882, issued to Luther on Apr. 28, 1998 and entitled "NEEDLE BLUNTING ASSEMBLY FOR USE WITH INTRAVASCULAR INTRODUCERS", discloses a non-automatic manual needle blunting assembly which features a blunting member disposed telescopically within the passageway of a needle or cannula and manually axially movable from a "non-blunting" position to a "blunting" position. In alternative embodiments, the blunting member is held in place by screw threads or elastomeric fins within a chamber defined by the needle member. The referenced needle is neither automatic in operation nor lockable, the user manually advances or retreats the blunting assembly and the positioning can be altered by an accidental bump.

U.S. Pat. No. 5,374,252 to Banks et al, dated Dec. 20, 1994 and entitled "LOCKING PNEUMONEEDLE", discloses a pneumoneedle used for introducing an insufflating gas into the abdominal cavity of a patient via the fluid conduit. The device comprises a cannula (20) (FIG. 1) mounted in a housing (12). The housing (12) also contains a tubular protector (or "blunting member") (31) disposed within the cannula and movable between a retracted position in which the sharp tip of the cannula is exposed and a deployed position in which the blunt end (32) of the protector extends beyond the sharp tip of the cannula. The protector (31) is tubular and has a distal aperture (36) that is exposed when the protector is moved to the deployed position. There is also a proximal aperture (35) that opens to an internal fluid passageway portion of the housing (12). A fluid conduit (8) (FIG. 2) in the housing communicates with fluid passageway portion (18) and extends at an angle relative to the longitudinal axis of the needle cannula.

In the medical field, pneumoneedles such as those disclosed by Banks et al are considered to serve a function that is disparate from that of intravenous fluid flow devices and the knowledge in the art pertaining to pneumoneedles is not seen as analogous or pertinent to intravenous needles.

U.S. Pat. No. 5,250,036, issued to Farivar on Oct. 5, 1993 and entitled "INTRAVENOUS CATHETER PLACEMENT SYSTEM", teaches an intravenous catheter placement system having an external insertion guard tool assembly and a flexible catheter with an attachment at one end. Farivar does not teach a releasable locking mechanism.

U.S. Pat. No. 5,462,533, issued to Daugherty on Oct. 31, 1995 and entitled "SELF CONTAINED NEEDLE AND SHIELD", teaches a design having a cannula made up of two concentric tubes. First tube (12) comprises the puncture tip of the cannula, second tube (14) is mounted co-axially around first tube (12), and the two may be axially adjusted so as to withdraw the puncture tip of first tube (12) within second tube (14). The design allows latching of the cannula in the blunted position after use. Latching member (34)

comprises spring (44) having spring end (54) which engages with step (56) upon retraction of the puncture tip into the blunted position. However, no means is disclosed for disengaging spring end (54) from step (56) and thus releasing the needle from the blunted position back into a sharpened position. The mechanism is located within the apparatus, so access during use is impossible. It would be advantageous to allow the healthcare worker to re-use the self-blunting needle under certain circumstances. For example, despite the presence of a flash chamber to aid in locating a vein, occasionally the first puncture of the patient does not hit a vein and the needle must be re-inserted. During "intermittent administration," the user will use the same syringe to withdraw doses from a supply vial and administer them, several times.

It would also be advantageous to provide self-blunting needles which efficiently utilize the needle itself for fluid flow and which do not combine the function of blunting apparatus and catheter.

It would be advantageous to remove the possibility of accidental bumps or jostles changing the blunt or non-blunt configuration of the needle. It would also be advantageous to provide automatically self-blunting apparatus.

SUMMARY OF THE INVENTION

The present invention provides a needle assembly comprising a needle member comprising a needle cannula mounted in a housing, the needle cannula comprising a puncture tip and comprising a needle passageway extending substantially lengthwise through the needle cannula, and a blunting member comprising a blunting probe, the blunting probe comprising a blunt end, the blunting probe being disposed telescopically within the needle cannula while permitting flow through the needle passageway, the needle assembly being movable between a sharpened configuration in which the puncture tip of the needle cannula is exposed and a blunted configuration in which the blunt end of the blunting probe blunts the needle assembly. There is also a releasable locking means for releasably locking the needle assembly in the blunted configuration.

According to one aspect of the invention, the housing may define a chamber in fluid communication with the passageway of the needle cannula, and the releasable locking means may be located inside the chamber. In an alternative embodiment, the releasable locking means may be located outside the chamber. The housing may further define an open channel within which the releasable locking means is disposed.

According to another aspect of the invention, the releasable locking means may comprise a movable detent and a stay against which the detent may bear when the needle assembly is in the blunted configuration. The detent may be movable between a locking position in which it prevents the needle assembly from moving to the sharpened configuration and an unlocked position which permits the needle assembly to move to the sharpened configuration.

This invention also provides a needle assembly comprising a needle member comprising a needle cannula mounted in a housing, the needle cannula comprising a puncture tip and comprising a needle passageway extending substantially lengthwise through the needle cannula, the housing defining a chamber in fluid communication with the passageway of the needle cannula, the housing further defining an open channel comprising a stay. There is a blunting member comprising a blunting probe mounted in a shuttle, the blunting probe comprising a blunt end and being disposed telescopically within the needle cannula while permitting flow through the needle passageway. The blunting probe is movable between a sharpened configuration in which the puncture tip of the needle cannula is exposed and a blunted configuration in which the blunt end of the blunting probe blunts the needle assembly, and one of the shuttle and housing comprises a movable detent, and the other comprises a stay. The detent is movable between a locking position in which it may bear against the stay and prevent the needle assembly from moving to the sharpened configuration and an unlocked position which permits the needle assembly to move to the sharpened configuration.

According to one aspect of this invention, the shuttle comprises the movable detent. Optionally, the detent may extend outside the housing. Also optionally, the detent further comprises a coupling site.

This invention further provides a needle assembly comprising a needle member comprising a needle cannula mounted in a housing, the needle cannula comprising a puncture tip and comprising a needle passageway extending substantially lengthwise through the needle cannula, the housing defining a chamber in fluid communication with the passageway of the needle cannula, the housing further defining a stay outside the chamber. There is also a blunting member comprising a blunting probe mounted in a shuttle, the shuttle carrying a movable detent, the blunting probe comprising a blunt end, the blunting probe being disposed telescopically within the needle cannula while permitting flow through the needle passageway, and being movable between a sharpened configuration in which the puncture tip of the needle cannula is exposed and a blunted configuration in which the blunt end of the blunting probe blunts the needle assembly. The detent is movable between a locking position in which it may bear against the stay and prevent the needle assembly from moving to the sharpened configuration and an unlocked position which permits the needle assembly to move to the sharpened configuration, and the movable detent comprises a coupling site for engagement by an accessory. Optionally, the housing may define an open channel and the stay may be disposed within the open channel.

This invention further provides an accessory-needle apparatus comprising a needle assembly as described above together with an accessory dimensioned and configured to engage and move the detent to the unlocked position when the accessory engages the needle member The accessory may be selected from the group consisting of a catheter, a Y-line adapter and a medication vial.

According to a particular embodiment, a detent as described herein may comprise an oblique flange, dimensioned and configured such that when the coupling site engages the accessory, the detent moves to the unlocked position.

In another embodiment, this invention provides a safety needle assembly comprising (i) a needle member comprising a needle cannula, the needle cannula having a puncture tip and having a needle passageway extending substantially lengthwise, and further comprising an interior; (ii) a blunting member comprising a blunting probe having a blunt end and having a sharpened blood collection end suitable for insertion into a blood collection tube and having a blunting member passageway extending from the blunt end to the blood collection end, and further comprising a shuttle; and (iii) the blunting member being disposed telescopically within the needle cannula while permitting fluid communication from the needle passageway to the blunting member passageway, and being movable between a sharpened configuration in which the puncture tip of the needle cannula is exposed and a blunted configuration in which the blunt end of the blunting probe blunts the safety needle assembly, wherein the needle member and the shuttle are dimensioned and configured for releasably locking the safety needle assembly in the blunted configuration.

There is also provided a blood collection needle comprising a holder dimensioned and configured to receive therein at least one end of a blood collection tube and a safety needle assembly as described herein mounted on the holder comprising a needle cannula mounted in a housing, wherein the holder comprises means for moving the blunting probe between the sharpened configuration and the blunted configuration.

According to one embodiment of the invention, the means for moving may comprise a longitudinal slot in the holder and first and second locking regions extending therefrom and a transmitting sleeve slidably disposed within the holder. The sleeve may comprise a tab protruding from the holder through one of the slot and the first and second locking regions, and may further comprise a swiping ring dimensioned and configured to unlock the safety needle assembly when the tab is moved from a locking region to the slot, and to lock the safety needle assembly when the tab is moved from the slot to a locking region.

There is further provided, in an alternative embodiment of this invention, a needle assembly comprising a needle member comprising a needle cannula mounted in a housing, the needle cannula comprising a puncture tip and comprising a needle passageway extending substantially lengthwise through the needle cannula, and a blunting member comprising a blunting probe mounted in a shuttle wherein the shuttle is disposed in the housing. The shuttle comprises a body and a movable detent, the detent comprising a base, the body and the base each having an aperture therein, a base aperture having an outlet and a body aperture having a guide surface that is offset from but converges to the body aperture. The blunting probe is disposed telescopically within the needle cannula while permitting flow through the needle passageway, and is movable between a sharpened configuration in which the puncture tip of the needle cannula is exposed and a blunted configuration in which a blunt end of the blunting probe blunts the needle assembly. The housing defines a first shoulder thereon and the shuttle is dimensioned and configured so that the detent can engage the first shoulder when the apparatus is in the blunted configuration and the detent is in the locking position. The detent is movable between a locking configuration in which the base aperture outlet is aligned with the guide surface and a released configuration in which the base aperture outlet is aligned with the body aperture.

Optionally, the housing may define a groove providing a second shoulder against which the detent may bear when the arm is in the locking position and the needle assembly is in the sharpened configuration.

There is further provided, in yet another embodiment of this invention, a blunting member comprising a blunting probe mounted in a blunting member hub, wherein the probe has a blunt end and a blood collection end and a blunting member passageway extending from the blunt end to the collection end, the blunting member further comprising an interior. There is also a needle member comprising a needle cannula, the needle cannula having a puncture tip and with a needle passageway extending substantially lengthwise through the cannula, and the needle member further comprising a needle shuttle on which the cannula is mounted, the needle shuttle being disposed telescopically within the blunting member interior, the blunting probe being disposed telescopically within the needle cannula. The needle shuttle is movable between a releasably locked sharpened configuration in which the puncture tip of the needle cannula is exposed and a releasably locked blunted configuration in which the blunt end of the blunting probe blunts the needle assembly.

BRIEF DESCRIPTION OF THE DRAWINGS

FIG. 1A is a schematic, partially cross-sectional view of a needle member configured for use in a particular embodiment of the present invention;

FIG. 2A is a schematic cross-sectional view of a particular embodiment of a blunting member for use with the needle member of FIG. 1A;

FIGS. 5A and 5B are schematic cross-sectional views of a self-blunting catheter assembly in accordance with one embodiment of the invention, comprising the needle assembly of FIG. 3 in the blunted and released configurations, respectively;

DETAILED DESCRIPTION OF THE INVENTION AND PREFERRED EMBODIMENT THEREOF

The present invention provides a self-blunting medical needle device that may be locked in a blunted configuration before and after use and which, even during some modes of use, does not expose a sharpened needle to the healthcare worker. The locked configuration may be released during use, but need not be released at other times. Accordingly, the likelihood that an inadvertent needle stick will occur is significantly reduced. For example, a needle device according to the present invention may be locked in a blunted configuration until the needle is fully inserted into an accessory device such as a catheter, an intravenous line Y-connector, a medicine supply vial, etc. In such case, the needle assembly is not sharpened until the last possible moment and, in many instances, the sharp tip of the needle need not be exposed to the user at any time during use. In embodiments of the invention, the device is used in a sharpened configuration, e.g., as an introducer needle for a catheter or guide wire, and is locked in the blunted configuration thereafter. The device may be releasably locked in the blunted configuration so that it can be re-sharpened and re-used, if necessary.

Figure 1B:
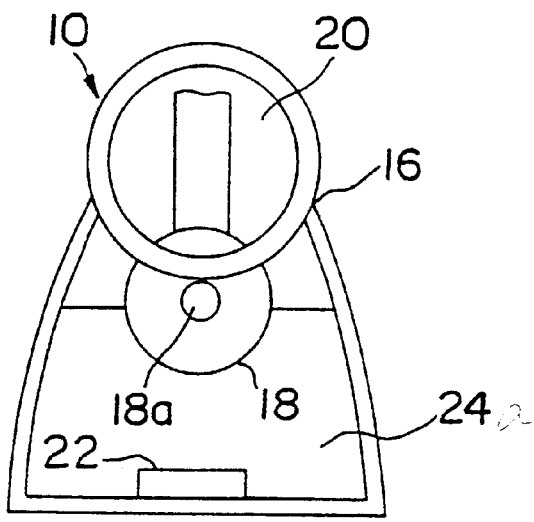
FIG. 1B is a schematic elevational view of the needle member of FIG. 1A, taken along line 1B—1B.

One embodiment of a component of a needle device in accordance with the present invention is shown in FIGS. 1A and 1B. The illustrated component is a needle member 10 that comprises a needle cannula 12 mounted in a housing 16. Needle cannula 12 has a sharp puncture tip 14 for penetrating a patient's skin and other tissues and a passageway that extends through the cannula and which opens into a chamber 16a in housing 16. Needle member 10 is preferably dimensioned and configured to facilitate the handling of needle cannula 12 for convenient connection to other devices and may include structural features intended for specific environments of use. For example, when the device is intended for use in introducing a venal or arterial catheter, housing 16 may comprise a flash chamber 20 into which blood can flow from needle cannula 12 to signal the user that needle cannula 12 is properly positioned. Optionally, chamber 20 may be configured to receive other devices such as a dosage syringe or fluid delivery tube.

Needle member 10 may be configured to engage a blunting member in a locked blunted configuration. In the illustrated embodiment, needle member 10 comprises a stay 22 that will engage a blunting member as described below. Stay 22 may be positioned at any convenient point on needle member 10 but, in the illustrated embodiment, stay 22 is formed as the shoulder at the end of a sloped incline in a U-shaped guide 24 that is on housing 16 but outside of the chamber 16a.

Needle member 10 defines a blunting probe aperture 18a which is preferably fitted with a bushing 54, for receiving the blunting member and through which a blunting probe may be inserted into needle cannula 12 via chamber 16a, as described below. Bushing 54 is an O-ring providing both a sealing function and a guiding function.

Figure 2B:
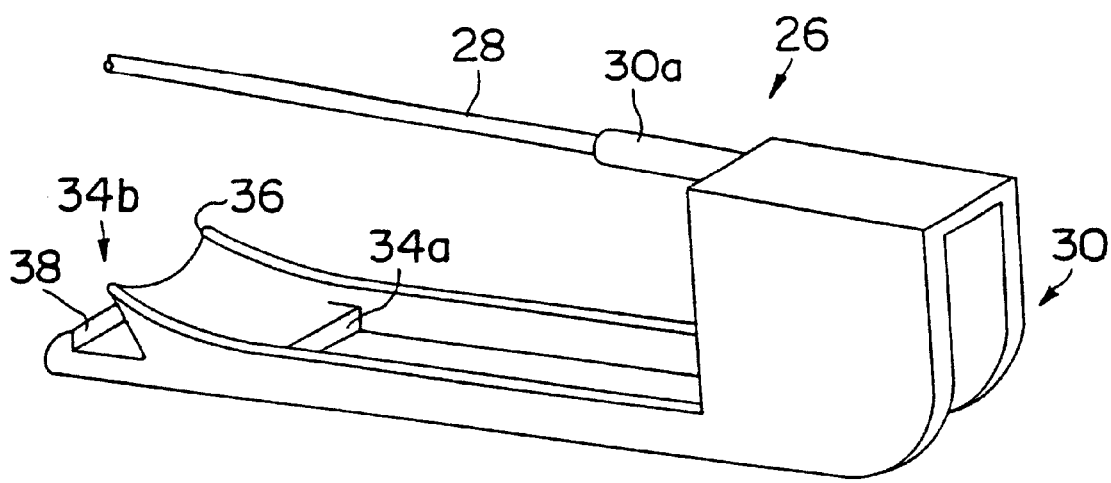
FIG. 2B is a perspective view of a blunting member intended for use with the needle member of FIG. 1A.

A blunting member suitable for use with needle member 10 is shown in FIGS. 2A and 2B. Blunting member 26 comprises a blunting probe 28 that has a distal blunt tip 28a. Blunting probe 28 is carried on a shuttle 30. Shuttle 30 comprises a plunger portion 30a and a base portion 32 to which is connected a resilient, spring-like detent 34. Detent 34 is movable between a locking position in which it inhibits movement of the blunting member to an unlocked position in which it permits movement of the blunting member, as described further herein. Plunger portion 30a is configured to be movably received in blunting probe aperture 18a and to form a seal with aperture 18a about bushing 54. The plunger portion 30a thus extends into chamber 16a. Detent 34 extends outside of chamber 16a in the form of an arm and, in this particular embodiment, carries a lug 34a that is dimensioned and configured to engage stay 22 of needle member 10 (FIGS. 1A and 1B) as will be described below. Detent 34 also carries a coupling site 34b defined by an oblique flange 36 and a coupling shoulder 38.

Blunting probe 28 (FIG. 2A) is configured so that it can be inserted into probe aperture 18a and thus be telescopically disposed within needle cannula 12. Shuttle 30 (FIG. 2A) is dimensioned and configured so that when blunting probe 28 is thus inserted into needle cannula 12 (FIG. 1A), detent 34 can be received within and optionally fully surrounded by guide 24 and further so that it can move axially within channel 24a defined by guide 24. Shuttle 30 and guide 24 are dimensioned and configured so that detent 34 is biased against stay 22.

Figure 3:
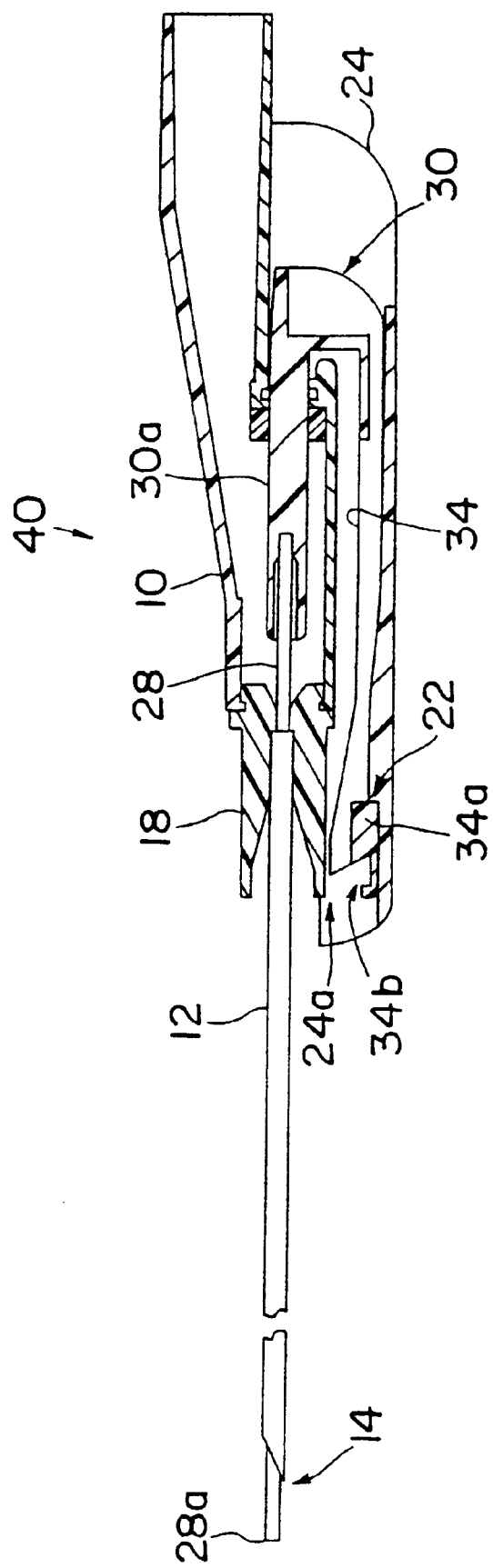
FIG. 3 is a schematic cross-sectional view of a needle assembly comprising the needle member of FIG. 1A and the blunting member of FIG. 2A.

When the needle assembly is in the blunted configuration, blunting member 26 acts to blunt needle member 10, for example, by extending to or beyond puncture tip 14. As indicated above, blunting member 26 is dimensioned and configured to fit within channel 24a of needle member 10, to produce a self-blunting needle assembly 40 shown in FIG. 3. FIG. 3 shows needle assembly 40 in the blunted configuration, i.e., with blunting probe 28 disposed telescopically within needle 12 and positioned therein so that blunt tip 28a protrudes beyond puncture tip 14 and thus blunts needle assembly 40. As illustrated in FIG. 3, lug 34a on blunting member 26 engages stay 22 on needle member 10. Accordingly, even if axial pressure is applied on blunt tip 28a, movement of blunt tip 28a into needle cannula 12 (exposing puncture tip 14) is prevented because lug 34a of detent 34 bears against stay 22, thus preventing rearward axial movement (as sensed relative to needle cannula 12) of blunting probe 28. Thus, needle assembly 40 is locked in the blunted configuration.

However, needle assembly 40 is releasably locked in the blunted configuration. To release the blunting member in needle assembly 40 as shown in FIG. 3, it is necessary to disengage lug 34a from stay 22. In the particular illustrated embodiment, guide 24 is dimensioned and configured to permit the flexure of detent 34 to permit lug 34a to be moved upward (as sensed in FIG. 3) for a distance sufficient to disengage lug 34a from stay 22. Once detent 34 has been flexed in this manner, blunting member 26 is free to slide within guide 24 for a distance sufficient for blunt tip 28a to be withdrawn into needle cannula 12, thus exposing puncture tip 14.

Figure 4A:
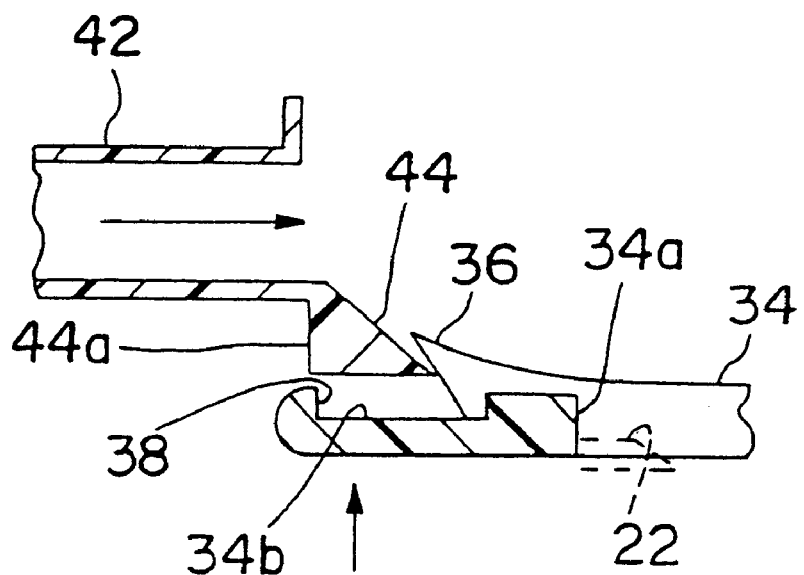
FIGS. 4A and 4B are schematic cross-sectional views illustrating the operation of a release accessory with the detent of the blunting member of FIG. 2A.
Figure 4B:
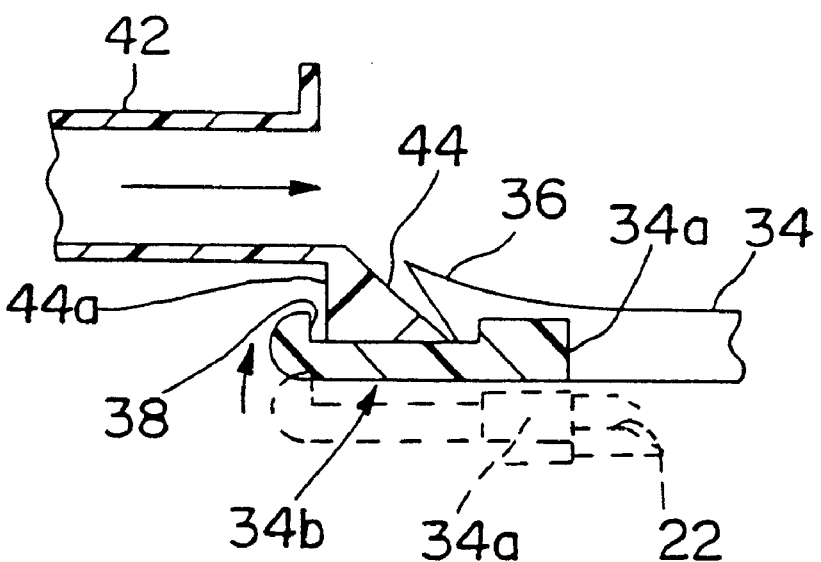

Guide 24 is open-ended so that detent 34 is accessible from outside guide 24. Coupling site 34b on detent 34 is especially accessible and is dimensioned and configured to engage an accessory device that is used to raise lug 34a away from stay 22. A suitable accessory is partially illustrated in FIGS. 4A and 4B. Accessory 42 carries a pawl 44 that is dimensioned and configured to enter channel 24a (FIG. 3) and to engage coupling site 34b. In particular, pawl 44 initially engages flange 36. Due to the slanted internal configuration of flange 36, movement of accessory 42 in a substantially axial direction causes flange 36 to rise, as sensed in FIG. 4A, thus flexing detent 34 and lifting lug 34a, as indicated by the unnumbered arrows in FIG. 4A. Flange 36 and coupling site 34b are dimensioned and configured so that the axial movement of accessory 42 flexes detent 34 to a degree sufficient to disengage lug 34a from stay 22 (shown in FIG. 3). When pawl 44 is fully received within flange 36, a coupling surface 44a on pawl 44 is disposed against coupling shoulder 38, as shown in FIG. 4B, which shows the elevated, disengaged (i.e., released) position of detent 34 and, in dotted outline, the locked position of detent 34. One advantage of the illustrated embodiment is that the releasable locking mechanism is enclosed within guide 24, thus reducing the likelihood of inadvertent release of blunting member 26, that could lead to or allow an accidental needle stick.

In some embodiments, such as a Y-line connector, an accessory has an injection port dimensioned and configured to receive the needle assembly and engage the coupling site. In other embodiments, such as a catheter, the catheter hub is dimensioned and configured to receive the needle assembly and engage the coupling site.

In a particular embodiment, an accessory may comprise part of a catheter assembly comprising a catheter hub on the end of a catheter tube. The catheter tube is sized to receive the needle cannula therein and the catheter hub is dimensioned and configured to engage the hub portion of the needle member. Thus, as shown in FIG. 5A, needle cannula 12, blunted by blunt tip 28a of blunting probe 28, is inserted into and through catheter hub 46b, which is dimensioned and configured to receive hub portion 18 of needle member 10. Hub 46b comprises an accessory flange 46c that is dimensioned and configured to enter U-shaped guide 24 and to engage the coupling site 34b on detent 34 as shown in FIGS. 4A and 4B.

The combination of catheter 46 and needle assembly 40 constitutes an accessory-needle apparatus in accordance with one embodiment of the present invention.

Catheter tube 46 and needle assembly 40 are dimensioned and configured so that, when catheter tube 46 is fully mounted on hub portion 18 of needle member 10, the end of catheter tube 46 is drawn past the puncture tip of needle cannula 12. To fully mount catheter tube 46 on needle assembly 40, catheter hub 46b is moved axially along needle cannula 12. Such motion causes accessory flange 46c to engage coupling site 34b as shown in FIGS. 4A and 4B. Once accessory flange 46c engages coupling site 34b, the initial rearward axial motion of catheter hub 46b disengages lug 34a from stay 22. Further axial motion of catheter tube 46 towards full engagement with needle member 10, as shown in FIG. 5B, moves blunting member 26 rear-wardly (i.e., away from puncture tip 14 of needle cannula 12) and draws blunt tip 28a of blunting probe 28 into needle cannula 12, thus exposing puncture tip 14. As indicated in FIG. 5B, blunting probe 28 is hollow and is equipped with venting port 48 that opens to flash chamber 20 of needle member 10. In another embodiment, blunting probe 28 is solid but is configured to permit flow through the needle cannula, e.g. it may define longitudinal flutes on its surface.

The fully assembled apparatus 50 is shown in FIG. 5B. The needle cannula 12 of apparatus 50 can be used to effect venipuncture using puncture tip 14 and to introduce catheter tube 46 into the vein. Proper positioning of needle 12 into the vein is indicated by the flow of blood through needle cannula 12, into hollow blunting probe 28, and through venting port 48 and access opening 52 in needle member 10 to flash chamber 20. As indicated above, needle member 10 comprises bushing 54 that is dimensioned and configured to engage shuttle 30 in a manner that permits movement of blunting member 26 between sharpened and blunted configurations while preventing fluid flow into U-shaped guide 24. This aspect of this invention thus pertains to a device in which a blunting member is disposed within a sealed chamber in the device, and is configured to extend from the interior of the sealed chamber to its exterior so that the blunting member can be manipulated by contact with a structure outside the sealed chamber without compromising the seal. In the embodiment illustrated, it is shuttle 30 which is dimensioned and configured for this purpose, but other embodiments will be obvious to those skilled in the art, after reading this disclosure.

After the catheter 46 is positioned as desired within the patient's vein, the needle assembly 40 is withdrawn from catheter 46. As needle member 10 is withdrawn from catheter hub 46b, accessory flange 46c pulls blunting member 26 forward in needle member 10 (i.e., towards puncture tip 14) by engaging coupling shoulder 38 (FIG. 4B). As lug 34a slides past stay 22 and needle assembly 40 is further withdrawn from catheter 46, lug 34a is moved into position to engage stay 22 and accessory flange 46c is disengaged from coupling site 34b. Accordingly, spring-like detent 34 moves downward, causing lug 34a to engage stay 22. This locks blunting member 26 in needle member 10 in the blunted configuration, i.e., with blunt tip 28a of blunting probe 28 extending beyond puncture tip 14. Due to the length of needle cannula 12 and blunting probe 28, needle assembly 40 becomes locked in the blunted configuration even before needle cannula 12 is fully withdrawn from catheter 46.

Figure 6:
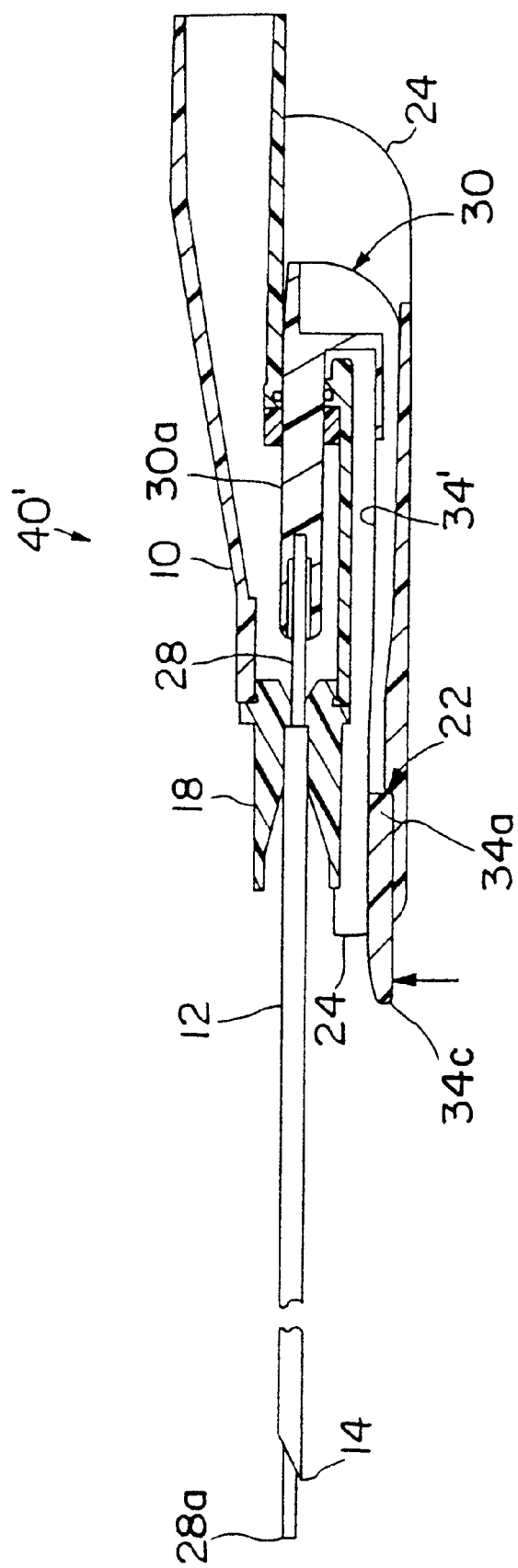
FIG. 6 is a schematic cross-sectional view of a needle assembly in accordance with yet another embodiment of the present invention in which an accessory device is unnecessary.

The location of stay 22 (FIG. 1A) and corresponding lug 34a (FIG. 2A) can be varied as matters of mere design choice. In addition, a variety of locking mechanisms that are releasable by the use of an accessory into which the needle is inserted can be employed. Another optional design choice is to configure the blunting member so that it can be disengaged from the needle member and moved between the sharpened and blunted configurations manually, as shown in FIG. 6. In the embodiment of FIG. 6, detent 34' and guide 24 are dimensioned and configured so that detent 34' extends beyond guide 24 to permit the user to disengage lug 34*a* from stay 22 (to move blunting member 26) without having to reach into channel 24*a*. Exposed portion 34*c* can be pressed towards needle cannula 12 to disengage lug 34*a* from stay 22 by applying finger pressure thereto. The user may then move blunting member 26 to the sharpened configuration by using his or her finger to move detent 34' rearward, i.e., away from puncture tip 14 of needle cannula 12, to prepare the device for use. Once needle cannula 12 is in place in the patient, the user may use his or her finger to move blunting member 26 into the blunted configuration, preferably with lug 34*a* engaging stay 22.

Still another manually-operable, releasably-lockable needle assembly in accordance with the present invention is seen in FIGS. 7A–7D.

Figure 7A:
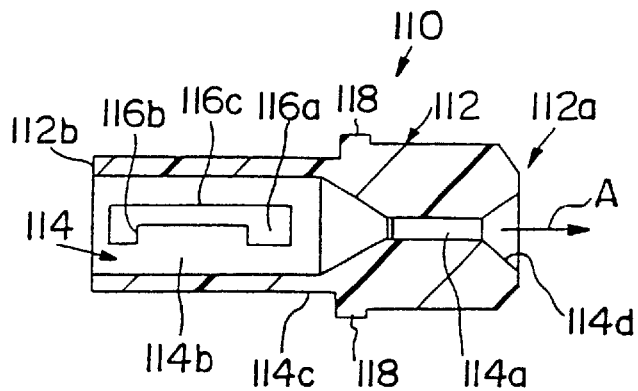
FIG. 7A is a cross-sectional view of a needle hub for holding a needle cannula in a blood collection device.

FIG. 7A shows a needle member 110 that comprises a generally cylindrical body 112 having a longitudinal axis A, a first end 112*a* and a second end 112*b*. Needle member 110 also comprises a circumferential locking flange 118 and at least one locking spline 120 (FIG. 7D) by which needle member 110 can be secured in a needle holder, as described below. The interior of needle member 110 comprises a hub passageway 114. The shuttle portion 114*b* of passageway 114 is dimensioned and configured to slidably receive a shuttle (FIG. 7B) therein. Body 112 defines two locking notches 116*a* and 116*b* and a channel 116*c* formed together as an aperture through the cylindrical wall of body 112. The mounting portion 114*a* of passageway 114 is dimensioned and configured to receive a needle cannula in the forward end thereof. The funnel-like insertion regions 114*c* and 114*d* at the ends of mounting portion 114*a* of passageway 114 converge from shuttle portion 114*b* and first end 112*a* of needle member 110, respectively, and facilitate the insertion therein of a blunting member and a needle cannula in assembly steps described below.

Figure 7B:
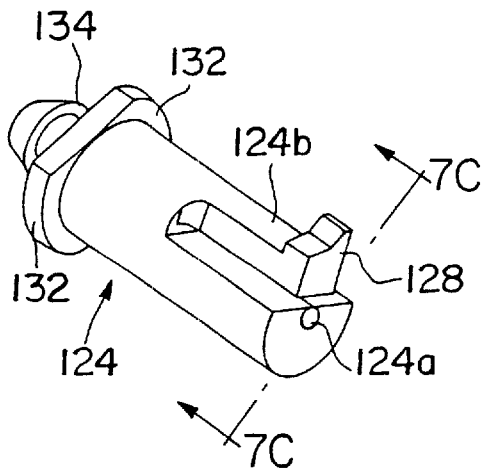
FIG. 7B is a perspective view of a blunting member shuttle intended for use with the needle hub of FIG. 7A.
Figure 7C:
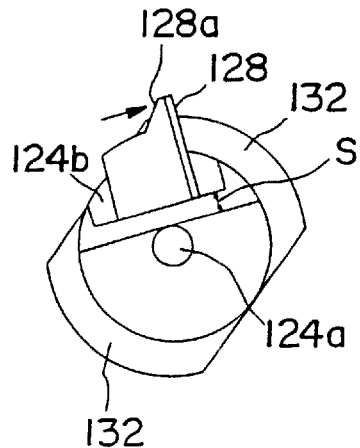
FIG. 7C is a view of the shuttle of FIG. 7B taken along line 7C—7C.

FIG. 7B shows blunting member shuttle 124 which has a generally cylindrical body that is dimensioned and configured to be slidably received within shuttle portion 114*b* of passageway 114 of hub 110, as will be described below. Shuttle 124 defines a central axial passageway 124*a* therethrough within which may be mounted a blunting probe. Shuttle 124 comprises a resilient, movable detent 124*b* that carries a lug 128. Resilient detent 124*b* suspends lug 128 at a stand-off from the remainder of the shuttle body, indicated as stand-off S in the end view of FIG. 7C. As is evident from FIG. 7C, lug 128 has protruding surface 128*a* that is disposed obliquely relative to the cylindrical periphery of shuttle 124. Therefore, a force applied upon surface 128*a* substantially along a tangent to the shuttle body (or parallel to such a tangent) can drive lug 128 in a radial direction (towards passageway 124*a*), narrowing stand-off S by flexing detent 124*b*.

Shuttle 124 comprises shuttle flanges 132 that permit shuttle 124 to engage another structure, as described below. Shuttle 124 also defines a boot barb 134 on which a self-sealing boot for sealing the sharpened insertion end 126*b* of blunting probe 126 may be anchored.

Figure 7D:
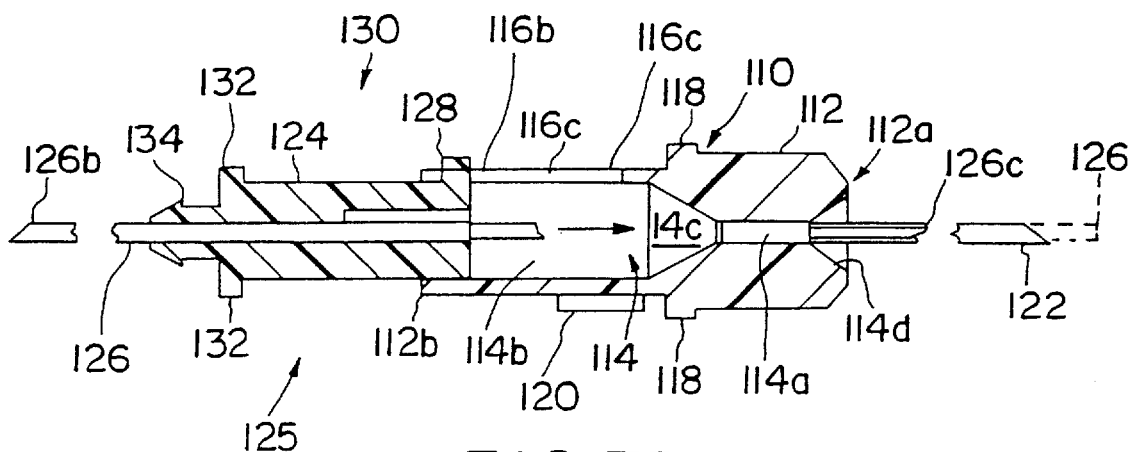
FIG. 7D is a cross-sectional view of a locking needle assembly comprising the hub and shuttle of FIGS. 7A and 7B with a needle cannula and blunting cannula secured therein.

FIG. 7D shows a safety needle assembly 130 that comprises needle member 110 and blunting member 125. Blunting member 125 comprises shuttle 124 and blunting probe 126. Needle cannula 122 has a blunt proximal end that is inserted into the first end 112*a* of needle member 110 and is secured therein by means of adhesive (not shown). The distal end of needle cannula 122 comprises a puncture tip. Passageway 114 defines a proximal insertion region 114*d* that converges rearward from first end 112*a* and thus facilitates the insertion of the blunt end of needle cannula 122 into passageway 114. The shuttle portion 114*b* of passageway 114 is dimensioned and configured to slidably receive shuttle 124 therein. A portion of blunting probe 126 extends forward from shuttle 124 through passageway 114 and into needle cannula 122, within which it is telescopically disposed and wherein it terminates at a first, blunt end. The forward extending portion of blunting probe 126 is referred to herein as blunt tip 126*a*. Sharpened insertion end 126*b* of blunting probe 126 engages a blood collection apparatus (not shown). Blunting probe 126 and needle cannula 122 cooperate to form a fluid flow passageway that extends through both of them. Thus, blunting probe 126 and needle cannula 122 are disposed telescopically one within the other, while permitting flow through the needle passageway. Preferably, but not necessarily, insertion region 114*c* converges to a diameter that is smaller than the internal diameter of needle cannula 122 and is aligned therewith so as to provide a stop for the insertion of needle cannula 122 into body 112, as well as guiding blunt tip 126*a* of blunting probe 126 into the proximal end of needle cannula 122. Blunting probe 126 also extends rearward from shuttle 124, terminating at second, sharp insertion end 126*b* (sometimes referred to herein as a "filling needle") for puncturing the seal on a collection tube and for providing a conduit to establish fluid flow communication between the collection tube and needle cannula 122, as will be described below. Blunting probe 126 is securely mounted within shuttle 124 so that it moves with shuttle 124.

Lug 128 on shuttle 124 is dimensioned and configured to protrude through, and to be secured within, locking notches 116*b* and 116*a* (FIG. 7A), to secure the relative positions of blunting member 125 and needle member 110. FIG. 7D shows needle assembly 130 in an insertion configuration (sometimes referred to herein as the "sharpened configuration"), in which blunting member 125 is in a retracted position in needle member 110. As shown, assembly 130 is locked in the sharp configuration by the engagement of lug 128 in rear locking notch 116*b*. Pressing lug 128 into passageway 114 disengages lug 128 from notch 116*b* so that blunting member 125 may be advanced within passageway 114. Lug 128 can slide along channel 116*c* until it engages forward locking notch 116*a*, thus securing blunting member 125 in an advanced or extended position within needle member 110, resulting in a blunted configuration in which blunting tip 126*a* protrudes beyond the sharp tip of needle cannula 122 (as indicated in dotted outline), blunting the needle assembly.

Figure 8A:
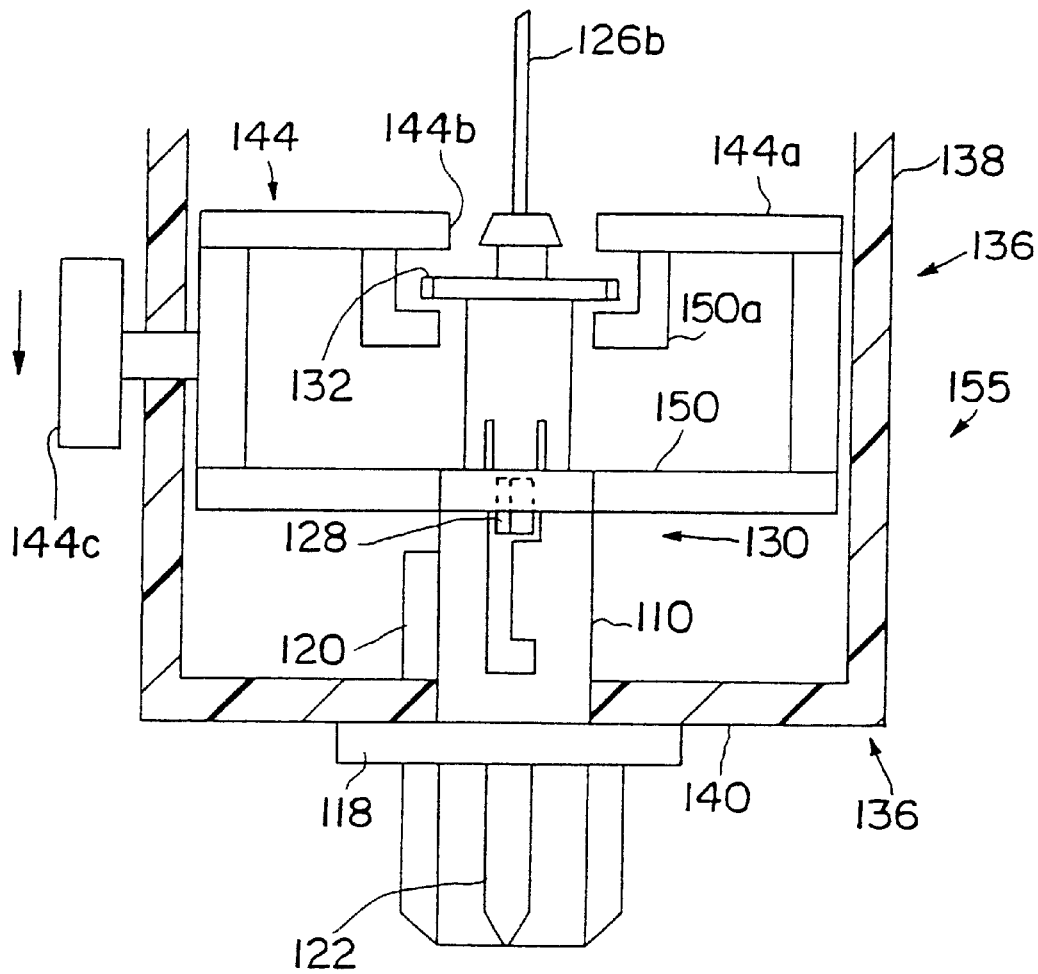
FIG. 8A is a schematic partial cross-sectional view of a collection needle assembly comprising the needle assembly of FIG. 7D in accordance with another embodiment of the present invention.
Figure 8B:
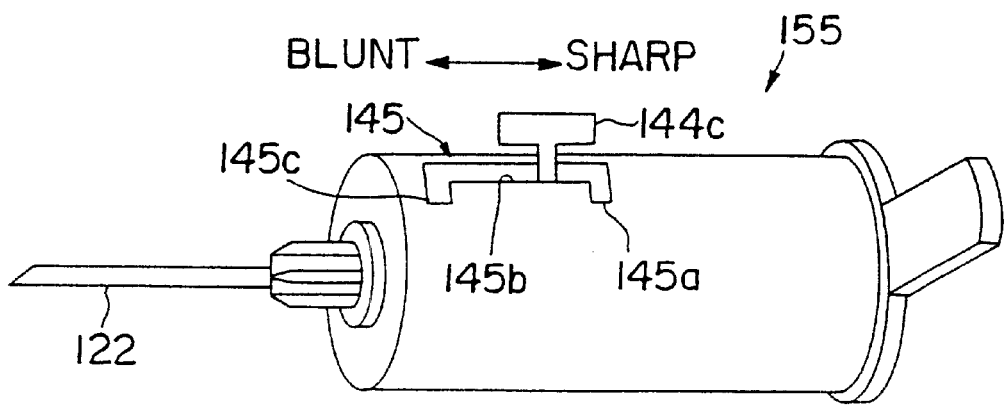
FIG. 8B is a perspective view of the collection needle assembly of FIG. 8A.

Blood collection needle 155 comprising needle assembly 130 of FIG. 7D is seen in FIGS. 8A and 8B. One embodiment of blood collection needle 155 in accordance with the present invention is shown in FIG. 8A. Blood collection needle 155 includes holder 136 that comprises cylindrical shell 138 that defines a needle aperture at its forward end 140. The needle aperture is dimensioned and configured to receive needle assembly 130 of FIG. 7D. The aperture defines notches (not shown) that are sized to allow spline 120 and lug 128 to pass therethrough as needle member 110 is inserted into the aperture. Forward end 140, however, is dimensioned and configured to engage hub flange 118 of needle assembly 130 (FIG. 7D). Forward end 140 may be configured to be received in a friction fit between flanges 118 and spline 120 when needle member 110 is inserted into the needle aperture as far as flange 118 will permit, and then rotated to move spline 120 out of alignment with the notch that permitted its entry into shell 138. A stop lug (not shown) is positioned in shell 138 to engage spline 120 upon such rotation and thus limit the rotation to a suitable turn, e.g., 45 degrees. Needle assembly 130 may thus be mounted in holder shell 138.

Figure 8C:
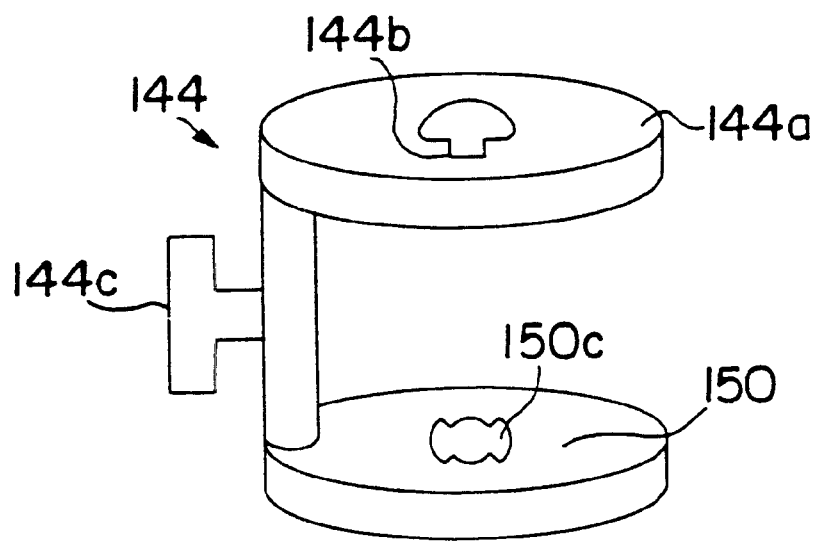
FIG. 8C is a perspective view of the transmitting sleeve seen in FIG. 8A.
Figure 8D:
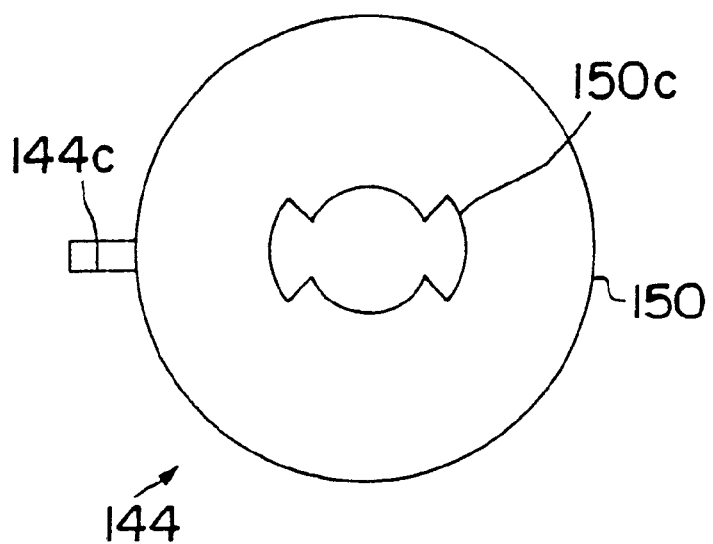
FIG. 8D is a end view of the transmitting sleeve seen in FIG. 8A.

Shell 138 contains transmitting sleeve 144 which is slidably disposed in the interior of shell 138. Transmitting sleeve 144 has at its coupling end 144a access aperture 144b. Coupling end 144a is dimensioned and configured to engage the filling end of a conventional collection tube and aperture 144b permits sharpened insertion end 126b of blunting probe 126 (FIG. 7D) to protrude through coupling end 144a and into a collection tube. Transmitting sleeve 144 also comprises flange 150a that engages flange 132 on shuttle 124. Transmitting sleeve 144 further comprises swiping ring 150 that is connected to coupling end 144a. The interior of swiping ring 150 (including flange 150a and swipe ring aperture 150c (FIG. 8C)) is dimensioned and configured to permit the insertion and rotation of needle assembly 130 therein as is necessary to mount needle assembly 130 in shell 138, without depressing lug 128 (FIG. 7D). Push tab 144c is attached to transmitting sleeve 144 and extends through slot 145. Shell 138 allows for convenient manual manipulation of transmitting sleeve 144, as described below. FIGS. 8C and 8D show two views of transmitting sleeve 144, showing swipe ring aperture 150c which engages lug 128 when transmitting sleeve 144 is rotated.

FIGS. 8A and 8B show blood collection needle 155 in an initial configuration in which needle assembly 130 is in a sharpened configuration.

To prepare blood collection needle 155 for use, a technician will typically install needle assembly 130 in holder 136 as shown in FIG. 8B, and then remove from needle cannula 122 a protective sheath (not shown) and insert needle cannula 122 into a patient's vein. Then, the user may take a conventional collection tube (not shown) and insert the capped end thereof into the open end of shell 138 with sufficient force to assure that sharpened insertion end 126b of blunting probe 126 punctures the seal cap on the collection tube and advances the collection tube until it engages coupling end 144a, thus establishing flow communication between the collection tube and the needle assembly. Shuttle 124 resists being moved forward into hub 110 because lug 128 is locked in notch 116b (FIG. 7D). After the collection tube fills with blood, the user may rotate tab 144c from a first locking region 145a in slot 145 to the travel region 145b and thus depresses lug 128 and unlocks needle assembly 130. Shuttle flanges 132 are then pushed by coupling end 144a so that blunt tip 126a of blunting probe 126 is extended beyond the tip of needle cannula 122, thus blunting the device. Rotation of tab 144c into second locking region 145c of slot 145 allows lug 128 to engage locking notch 116a so that blunting member 125 locks in the forward position with blunt tip 126a of blunting probe 126 extending beyond the puncture tip of needle cannula 122 before swiping ring 150 stops its forward movement. The process may be reversed: rotate tab 144c in second locking region 145c to unlock the needle assembly, move tab 144c rearward in travel region 145b to expose the puncture tip of needle cannula 122 and rotate tab 144c in first locking region 145a to allow the device to lock again in the sharp configuration.

Figure 9:
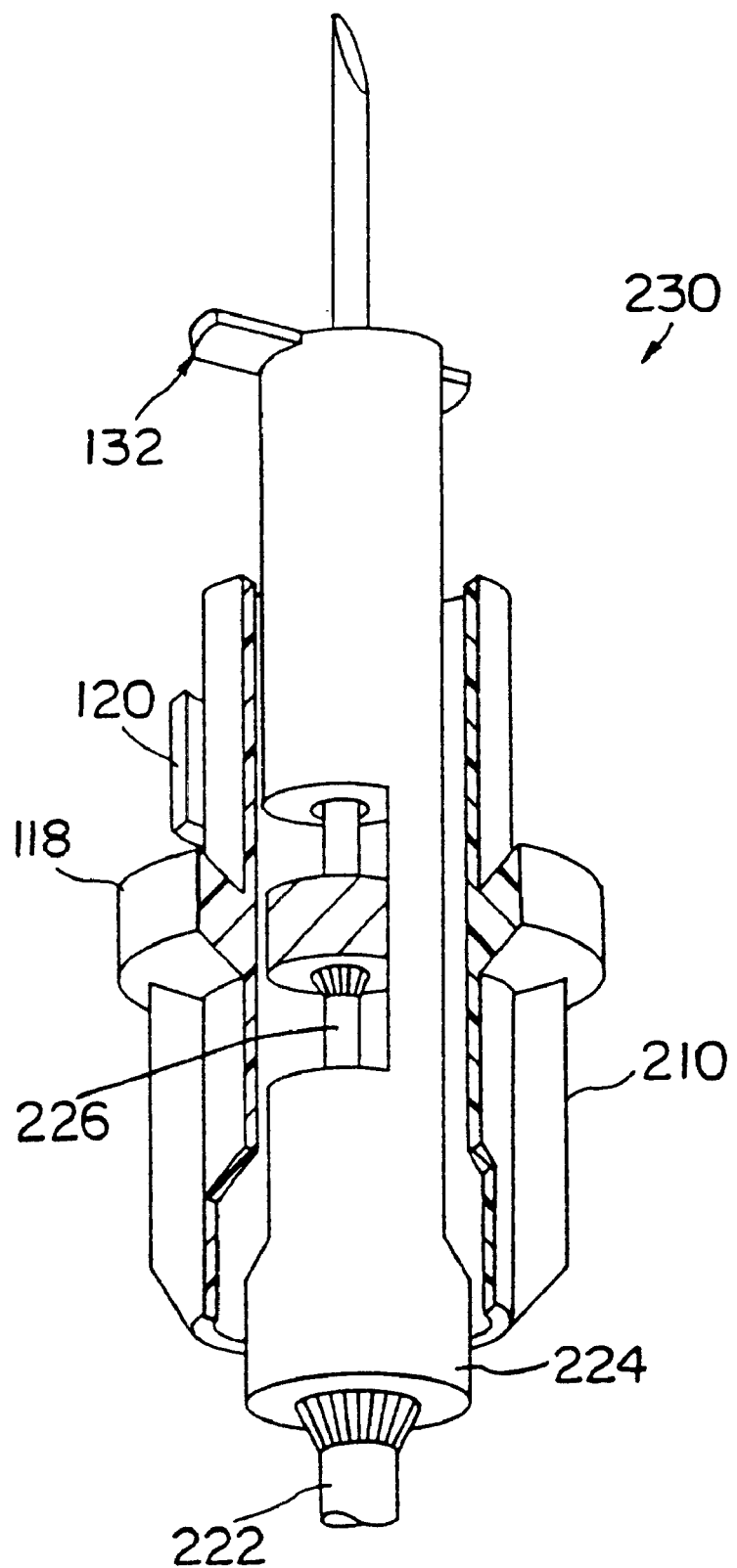
FIG. 9 is a schematic partially cross-sectional view of a locking needle assembly in accordance with yet another embodiment of the present invention.

In accordance with yet another embodiment of the present invention, a locking needle assembly may comprise a stationary blunting member and a movable needle. For example, safety needle assembly 230 shown in FIG. 9 comprises a blunting member that comprises a blunting probe 226 which is fixedly mounted in a blunting member hub 210. Received within blunting member hub 210 is a needle shuttle 224 on which a needle cannula 222 is mounted. Shuttle 224 and needle cannula 222 are configured so that blunting member 226 is disposed coaxially therewith. Shuttle 224 is movable within blunting member hub 210 between an extended position in which the insertion tip of needle cannula 222 extends beyond the blunt end of blunting probe 226 and a retracted position in which the blunt end of blunting probe 226 extends beyond the sharp tip of needle cannula 222. Blunting member hub 210 and shuttle 224 are releasably lockable by means of a lug and groove assembly like that described for needle assembly 130. Needle assembly 230 may be installed in a holder for use as a collection needle by securing blunting member hub 210 to the holder in a manner similar to that illustrated and described in connection with FIGS. 8A, 8B and 8C. It will be understood, however, that since the needle moves rather than the blunting member, moving tab 144c forward will extend the needle beyond the blunting member and thus sharpen the device, while moving tab 144c rear-ward will withdraw the needle and thus blunt the device. This is the opposite effect of that achieved by movement of the tab in the earlier discussed embodiment.

As previously indicated, the accessory that releases the needle assembly from the locked, blunted configuration may comprise a coupling site on any of a variety of medical devices, so that FIGS. 5A and 5B merely illustrate one particular embodiment of the invention. In other embodiments, the accessory may serve to couple needle assembly 40 to other needlereceiving devices such as anesthesia needles, biopsy needles, PICC and PTCA catheter introducers, guide wire introducers, and the like.

Figure 10:
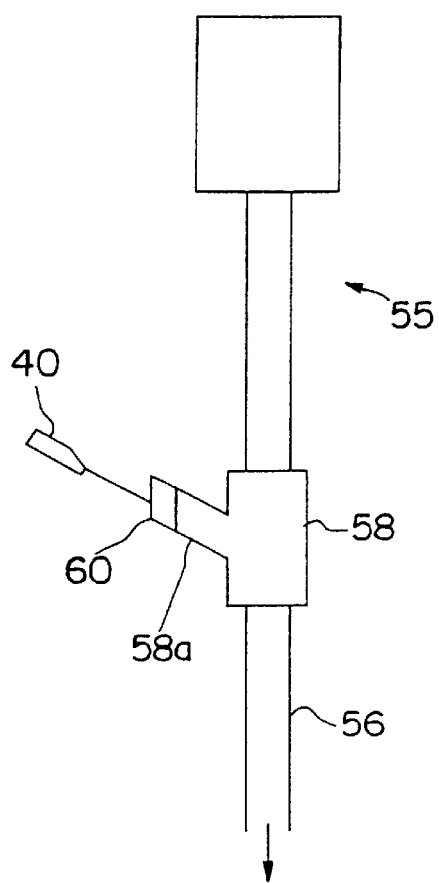
FIG. 10 is a schematic illustration of a y-line connector according to yet another embodiment of the invention.

FIG. 10 is a schematic diagram of an alternative embodiment of the invention in which needle assembly 40 is shown in IV (intravenous) apparatus 55. Y-line connector 58 has an arm 58a on which is located injection port 60. Injection port 60 is configured as shown in FIGS. 4A and 4B to engage with needle assembly 40 and reconfigure it from sharp to blunt when needle assembly 40 seats firmly against coupling port 60. By this means, needle assembly 40 may be used as shown to administer medication into IV line 56 leading to a patient, not shown. As will be obvious to those skilled in art, the accessory device may be a similarly configured member of numerous other classes of medical apparatus. For example, the accessory device could be a medicine vial, adapted to engage the accessory coupling portion of the needle assembly and thus re-sharpen the needle apparatus. This embodiment would be useful in, for example, an intermittent administration of medicine. Many other types of devices could be used, in many other situations and settings, without departing from the scope of the invention.

In other embodiments, the flow may be reversed and the invention used to safely withdraw liquids from an IV line.

Figure 11:
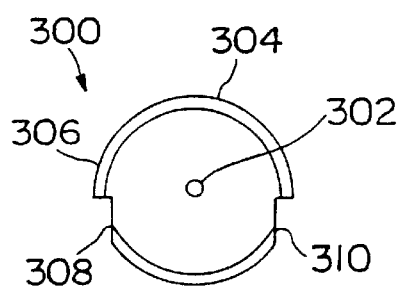
FIG. 11 is a frontal view of a catheter according to another embodiment of the invention.
Figure 12:
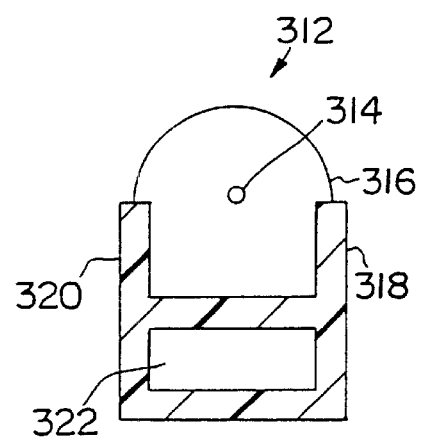
FIG. 12 is a cross-sectional frontal view of a needle member according to the embodiment of the invention illustrated in FIG. 11.
Figure 13:
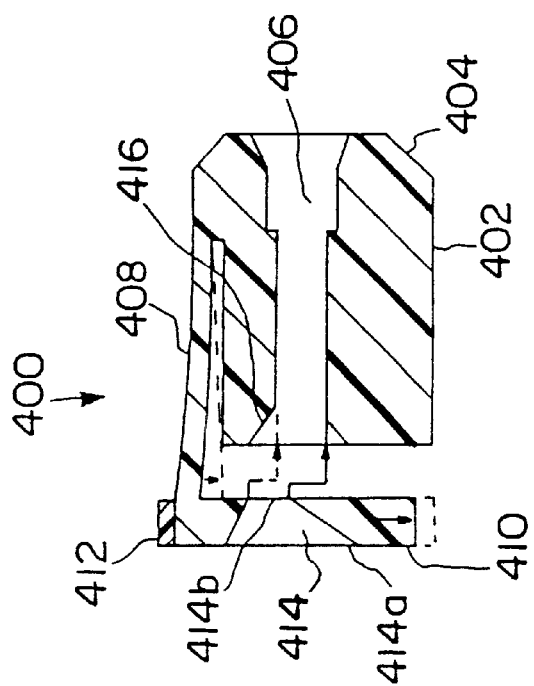
FIG. 13 is a cross-sectional side view of a shuttle of a blunting member according to another embodiment of the invention.

It will be understood from the foregoing that the interior of catheter hub 46b, Y-line connector 58, an injection port, a medicine vial or other accessory is dimensioned and configured to engage the exterior of needle hub 20a when the accessory device fully engages needle cannula 12. For example, when catheter 46 is fully seated on needle cannula 12, as illustrated in FIG. 5B, needle cannula 12 and catheter tube 46a are mutually aligned. Another feature of the present invention is that the accessory (here, catheter 46) and needle hub 20a are dimensioned and configured to substantially maintain their aligned orientation during a portion of the relative axial motion between them when needle cannula 12 is withdrawn from catheter hub 46b. For example, the two hubs may be configured with only a very slight taper, or they may have cylindrical surfaces dimensioned for a friction fit between them, and/or as shown in FIGS. 11 and 12, they may comprise a longitudinal flange and slot engagement between them, and they may engage each other over a substantially longer axial distance than conventional catheter hubs and needle hubs. In this way, as needle member 10 is withdrawn from catheter 46, catheter hub 46b maintains its alignment with needle hub 20a, with the result that catheter 46 and needle member 10 stay substantially aligned until needle cannula 12 is disposed well within catheter tube 46a and preferably, until the blunt tip of probe 28 has blunted puncture tip 14 of needle cannula 12. Thus catheter 46 and needle cannula 12 stay substantially aligned during the time that needle cannula 12 is withdrawn from the fully engaged configuration shown in FIG. 2 until the blunted configuration of FIG. 3 is attained, thus reducing the risk of injury to the patient. One embodiment for carrying out this feature of the invention is illustrated in FIGS. 11 and 12. FIG. 11 is a frontal view of a catheter according to the invention. Catheter 300 has catheter tube 302, catheter hub 304 and flange 306 disposed peripherally around catheter hub 304. Flange 306 has first notch 308 and second notch 310. Needle assembly 312 has needle cannula 314, hub 316, and channel 322, within which are the stay, lug and spring-like detent which releasably lock the device in the blunted configuration. First side wall projection 318 and second side wall projection 320 extend toward the axis of needle cannula 314. When catheter 300 is placed on needle assembly 312, first and second side wall projections 318 and 320 extend into second notch 310 and first notch 308 in the flange on catheter hub 304. When catheter 300 is slid off needle cannula 314, first side wall projection 318 and second side wall projection 320 block any rotational movement of catheter 300 relative to hub 316. Only when flange 306 clears the ends of first side wall projection 318 and second side wall projection 320 is rotation allowed.

A needle apparatus having another embodiment of a releasable lock mechanism is shown in FIGS. 13 through 17. The embodiment illustrated may be used in a guide wire introducer needle by which a physician can introduce into a patient a guide wire for a medical device to be inserted into a patient. For example, such a guide wire is commonly used to introduce a balloon catheter into a patient's coronary artery for balloon angioplasty. A locking, selfblunting guide wire introducer needle apparatus according to the present invention comprises a needle cannula as described above mounted in a housing and a blunting member mounted in a shuttle. Shuttle 400 (FIG. 13) has body 402, a front body bevel 404, a guide surface 416, a body aperture 406 and spring-like detent 408 in the form of an arm. Detent 408 is formed from a resilient material and, when unstressed, takes the unaligned position shown in solid lines in FIG. 13, i.e. detent 408 is distanced from body 402. Detent 408 carries a lug 412 and a base portion 410.

Through the middle of base 410 is first aperture (or base aperture) 414, which has base aperture outlet 414b sized to accommodate a guide wire. In the embodiment illustrated, first aperture 414 converges from an inlet 414a to outlet 414b to facilitate the insertion therethrough of a guide wire, as discussed further below.

At the rearward end of body 402 is a guide surface 416 which is offset from but converges toward aperture 406 from the rearward end of body 402. In an unaligned position, outlet 414b is aligned with guide surface 416, but not with the body aperture 406. A hollow blunting member 440 (shown in FIGS. 16 and 17) is inserted into body aperture 406 for mounting in body 402.

The needle cannula is mounted in a housing sized to receive the shuttle 400 therein and to provide shoulders against which lug 412 may bear. In the present embodiment, the needle housing is formed in two parts, a mounting portion 430 and a hub 418, both shown in FIG. 17. As seen in that Figure, hub 418 carries at least partial threads (unnumbered) or tabs for engaging the threads on a syringe 450 (shown in dotted outline). The interior of hub 418 is dimensioned and configured to receive shuttle 400 therein.

Figure 14:
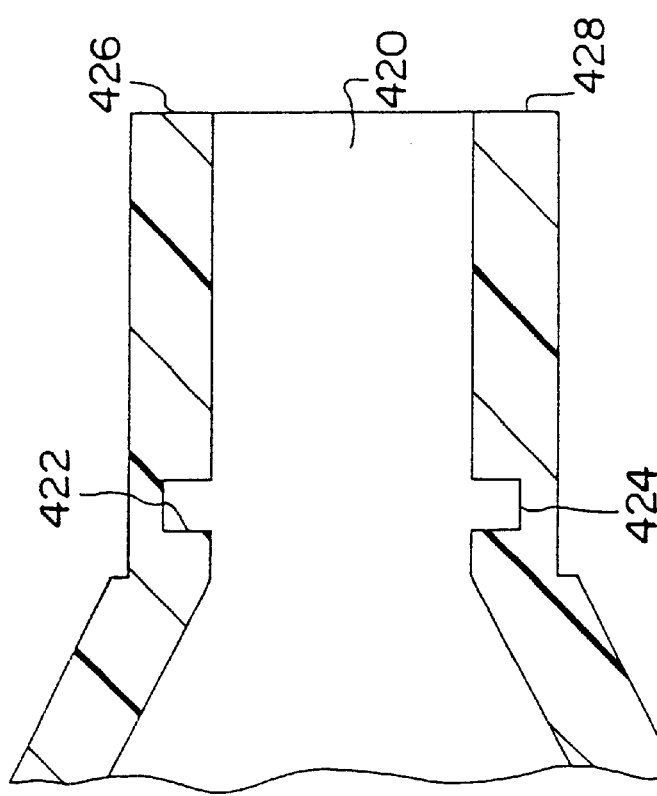
FIG. 14 is a cross-sectional side view of the locking portion of a needle hub according to the embodiment of the invention illustrated in FIG. 13.
Figure 15:
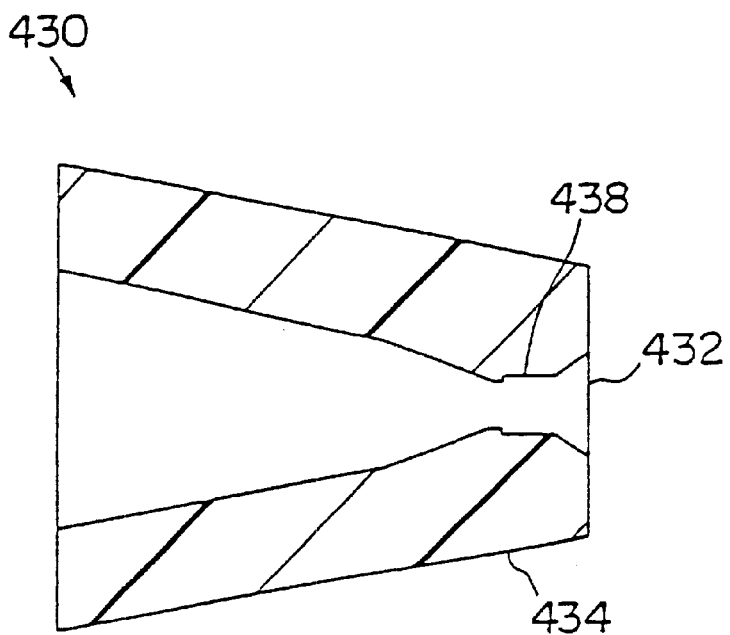
FIG. 15 is a cross-sectional side view of the nose portion of a needle hub according to the embodiment of the invention illustrated in FIG. 13.

The salient details of the interior of hub 418 are shown in FIG. 14. As the interior 420 of hub 418 defines an optional second shoulder 422, optionally formed by a groove 424, into which lug 412 may fall. Shuttle 400 has a forward shoulder 426. As suggested in FIG. 17, mounting portion 430 is configured to receive the forward end of hub 418 therein. When so assembled, shoulder 426 faces forward within the interior of mounting portion 430.

The needle member of this embodiment is assembled by mounting a needle cannula in mounting portion 430, a step which is facilitated by a bevel 432 (FIG. 15) in the mounting portion, and by securing the mounting portion onto the hub. The needle member is assembled by inserting a blunting probe into the forward end of shuttle 400. As suggested in FIG. 13, shuttle 400 defines an optional forwardly disposed shoulder in aperture 406 against which the blunting member may seat. The mounting of the needle cannula in mounting portion 430 and the mounting of the blunting probe in shuttle 400 are accomplished substantially as described in U.S. Pat. No. 5,951,520 to Burzynski et al, dated Sep. 14, 1999 and entitled "SELF-BLUNTING NEEDLE MEDICAL DEVICES AND METHODS OF MANUFACTURE THEREOF", the disclosure of which is hereby incorporated herein by reference.

Figure 16:
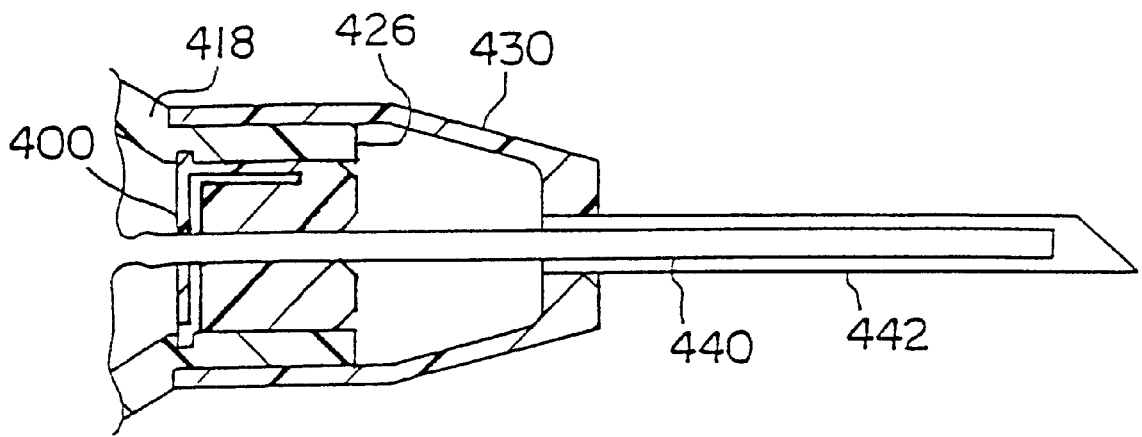
FIG. 16 is a partial cross-sectional side view of the invention according to the embodiment illustrated in FIG. 13.

The needle assembly is constructed as follows with reference to first FIG. 16. After the needle member is assembled by mounting needle cannula 442 in mounting portion 430 and securing mounting portion 430 to hub 418, the blunting member is inserted into the needle member so that blunting member 440 enters needle cannula 442. The blunting member is advanced until lug 412 falls into groove 424, as shown in FIG. 16. The apparatus is configured so that in this position the blunting probe does not extend beyond the tip of the needle, i.e., FIG. 16 shows the sharp configuration.

Figure 17:
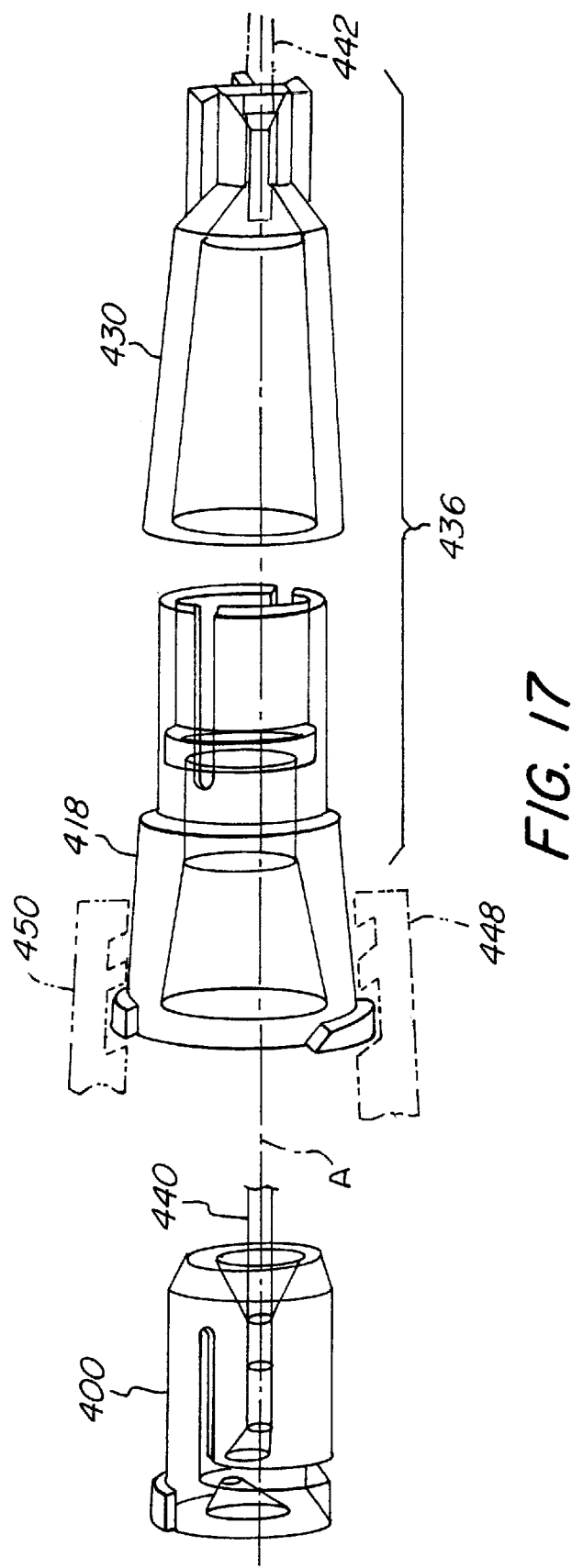
FIG. 17 is an exploded perspective view of the invention according to the embodiment illustrated in FIG. 13.

FIG. 17 shows the needle apparatus in exploded view. Needle cannula 442 is disposed within needle member 436, in bore 438. Insertion of needle cannula 442 into bore 438 is facilitated by bevel 432. Hub 418 is disposed inside needle member 436. Hub 418 and mounting portion 430 are axially aligned with needle cannula 442. Finally, hub 418 couples to syringe 450, which is partially shown in dotted lines. Threaded syringe nose 448 accepts hub 418.

Shuttle 400 is initially disposed within hub 418, with hollow blunting member 440 extending forward into needle cannula 442 but not extending beyond the tip, thus leaving needle cannula 442 sharpened. Detent 408, biased away from shuttle body 402, pushes lug 412 onto second shoulder 422 of circumferential groove 424.

In use, the needle assembly as shown in FIG. 16 is mounted on a syringe and is inserted into a patient until the tip is at the desired entry point for the guide wire. Syringe 450 is then removed, leaving the needle apparatus in place in the patient. A guide wire is then inserted through the apparatus of the embodiment. The guide wire is first threaded through first aperture 414 of base 410, and emerges from outlet 414b in alignment with guide surface 416. As the guide wire advances, guide surface 416 guides it into aperture 406 and through blunting member 440.

As one end of the guide wire moves along guide surface 416 towards body aperture 406, it pulls base aperture 414 downward (as sensed in FIGS. 13 and 17) into alignment with body aperture 406. Detent 408 is thus brought closer to body 402 against the bias of detent 408 and lug 412 is thus removed from second shoulder 422, releasing the invention from the locked configuration. Frictional force between the guide wire and blunting member 440 then acts to pull unlocked shuttle 400 forward, from hub 418 into needle mounting portion 430. This action extends blunting member 440 past the tip of needle cannula 442, blunting needle cannula 442 while it is in use inside the patient. When the guide wire is installed, the needle apparatus is removed from the guide wire. As the end of the guide wire passes through base 410, it releases detent 408, which springs away from shuttle body 402 so that lug 412 engages shoulder 426 to prevent rearward movement of the blunting member and lock the apparatus in the blunted configuration. Thus, as the apparatus is thereafter removed from the patient, it is locked in the blunted configuration.

Another optional feature of the present invention, which may be combined with other features of the invention or which may be practiced separately, pertains to the orientation of the locking means on the device. As suggested above, certain needle assemblies are designed to permit entry of the needle into a patient's tissue and to then rest against the patient's skin while permitting fluid flow therethrough. The surface of the device in contact with the patient's skin is referred to herein as the "contact surface" and it is typically a flat surface. However, the contact surface may be determined by the configuration of the device, even if it is not flat. For example, a winged intravenous needle device will be disposed with the wings against the patient's skin regardless of whether the surface of the device beneath the wings is flat. In some embodiments, there may be two areas on the device intended to serve as finger grip surfaces for a user and, in use, a surface of the device between the finger grips contacts the patient's skin and is the contact surface. In any case, the needle is typically parallel to the contact surface, and the closer the needle is to the contact surface, the more shallow the angle at which the needle can enter into and reside in the patient's skin and the lesser the risk of injury to the patient. The distance between the needle axis and the contact surface is referred to herein as the height of the needle in the device (indicated at H in FIG. 18B). In accordance with this optional feature of the invention, the locking mechanism is positioned so that it does not reside centrally between the needle and the contact surface of the device, but rather, the locking mechanism is positioned bliquely, e.g., beside the needle or above the needle (opposite from the contact surface). Therefore, the locking mechanism need not increase the height of the needle in the device or the angle of the needle from the patient's skin relative to a device without a locking mechanism, or it does so to a lesser degree than a device with a locking mechanism centered between the needle and the contact surface. By way of contrast, needle member 10 (FIG. 1B) has a channel between the contact surface of the device (the flat bottom surface in the Figure) and the needle, which will be concentric with the blunting probe aperture 18a. A similar arrangement is seen in FIG. 12.

In addition, such devices typically comprise a flash chamber and/or an access port where other fluid transfer devices such as a syringe, a luer connector, etc., may be connected. In prior art devices these structures are typically aligned with the needle and, because they are greater in diameter than the needle, they increase the height of the needle in the device. In devices according to this invention, such structures may be obliquely offset from the needle axis to keep the height of the needle at a minimum. Devices in which a flash chamber and/or access port are obliquely offset relative to the needle are described in detail in the Patent Cooperation Treaty application No. PCT/US99/24247, international filing date Oct. 15, 1999, which designated the U.S. and which is incorporated herein by reference.

Figure 18A:
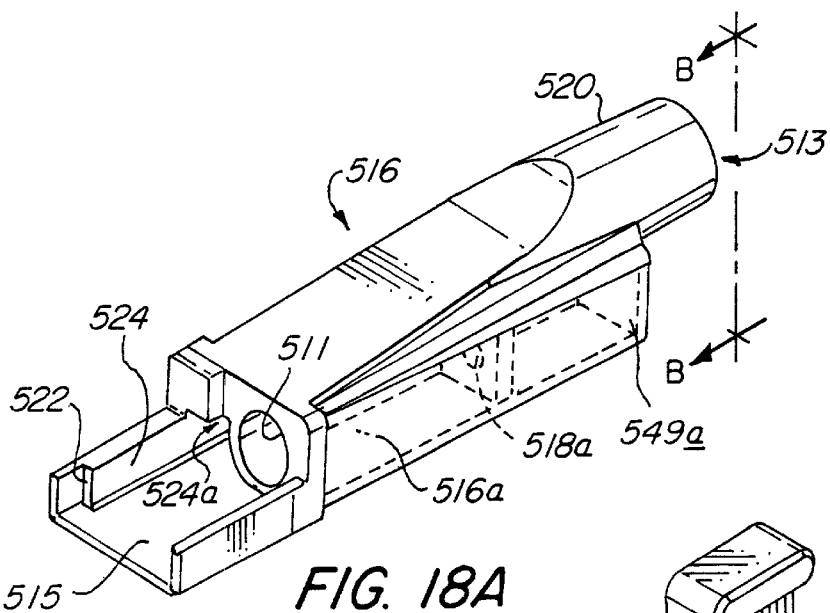
FIGS. 18A and 18B are perspective and elevation end views, respectively, of a housing for a needle assembly according to another embodiment of the present invention.

A housing for a needle assembly having obliquely positioned locking means is shown in FIG. 18A. Housing 516 defines an aperture 511 where a needle may be mounted (typically coaxially or concentrically with the center of aperture 511). Housing 516 defines a flat contact surface 548 which is between finger grip surfaces 549a and 549b (FIG. 18B) and beneath housing slide surface 515. Aperture 511 opens to a chamber 516a which is open to a flash chamber 520. Flash chamber 520 is formed from a translucent or transparent material and opens to an access port 513. Flash chamber 520 has an interior configuration which is at least partially cylindrical with a central axis which is offset from, but parallel to, the axis through the center of aperture 511 and parallel to surface 515. Access port 513 is typically circular and substantially parallel to aperture 511 but its center is obliquely offset from the center of aperture 511 relative to the contact surface of the device. Accordingly, the access port is obliquely offset from the needle relative to the contact surface of the device.

At the end of chamber 516a opposite aperture 511 is a blunting probe aperture 518a through which a blunting probe may be inserted into chamber 516a and thus into the needle cannula, as will be described further below. Housing 516 defines a channel 524a within which the locking mechanism resides. Channel 524a is beside aperture 511, instead of between aperture 511 and the skin contact surface of the device. Thus, disposing a locking mechanism in channel 524a does not increase the height of the needle in aperture 511 in the device, i.e., the locking mechanism will be obliquely offset from the needle relative to the contact surface. Housing 516 further defines a stay 522 on guide surface 524 to cooperate with the locking mechanism.

Figure 18B:
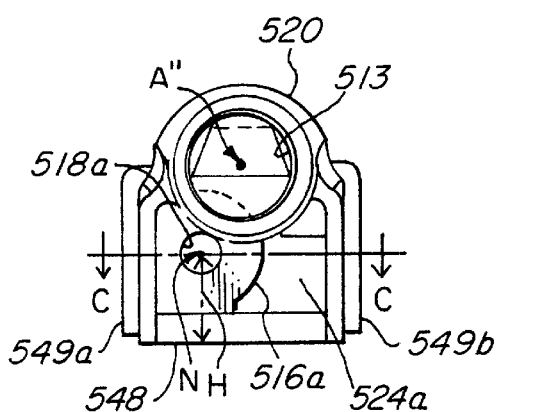

An end view of housing 516 is seen in FIG. 18B. In this view, the height of a needle (not shown) measured from contact surface 548 to needle axis N is indicated at H and it is clear that channel 524a is disposed beside (i.e., obliquely relative to) needle aperture 511 (FIG. 18A) so that the presence of any locking mechanism therein does not increase height H. It is also evident in FIG. 18B that the center of access port 513 and flash chamber 520, indicated at location A", is obliquely offset from needle axis N, so even though flash chamber 520 may be larger than chamber 516a, its presence in the housing does not increase height H.

Figure 18C:
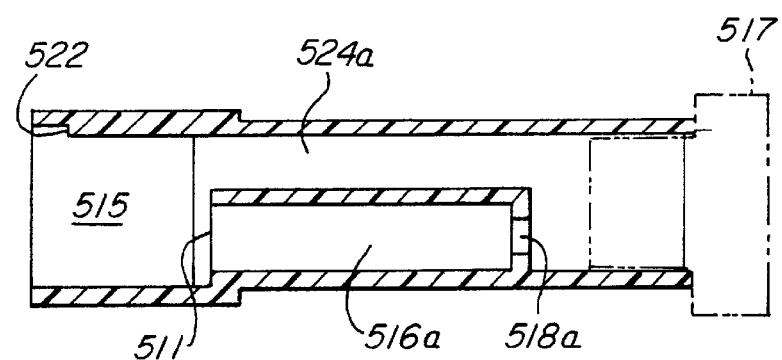
FIG. 18C is a cross-sectional view of the housing of FIG. 18B taken along line C—C.
Figure 19B:
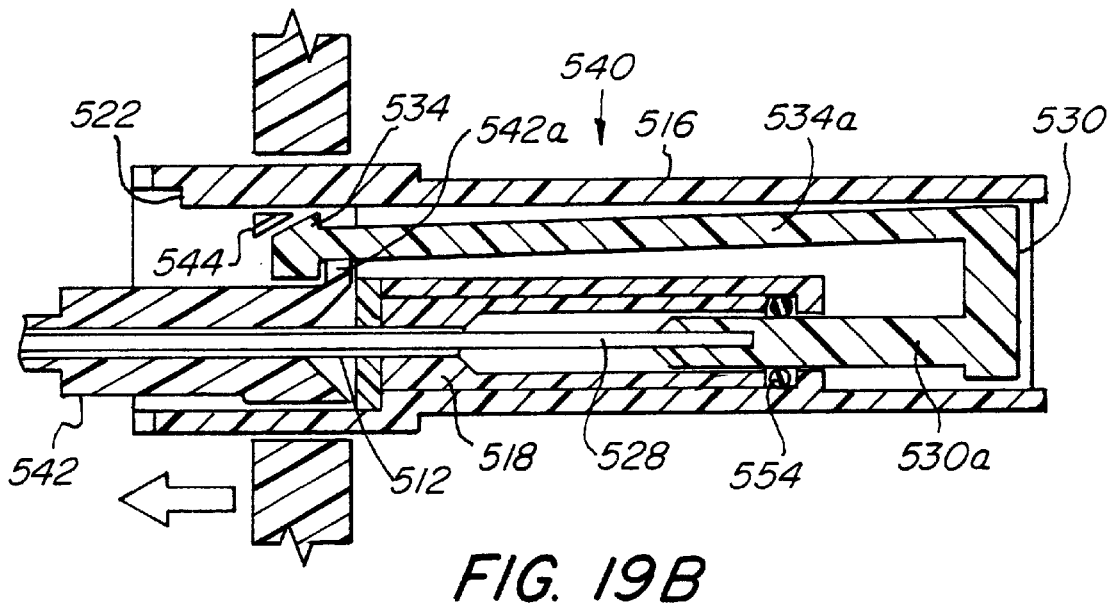
FIGS. 19A and 19B are partly cross-sectional views of a needle assembly in a blunted (FIG. 19A) and a sharpened (FIG. 19B) configuration.
Figure 19A:
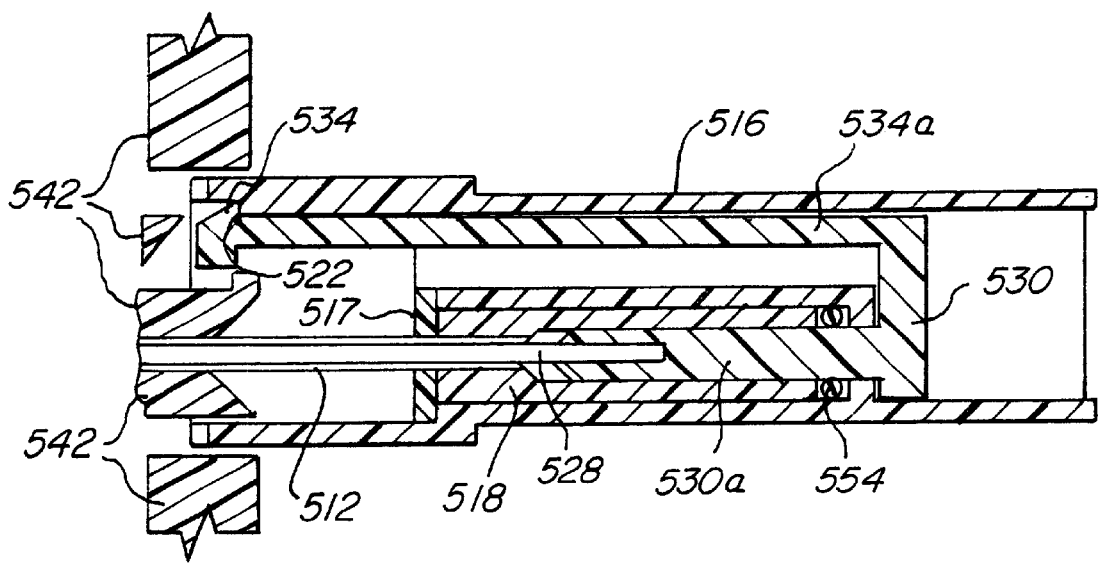

Housing 516 is intended for use as part of a needle assembly in which a needle cannula is mounted in aperture 511 so that the needle is parallel to slide surface 515 and contact surface 548. In addition, housing 516 accommodates a blunting member to produce a needle assembly 540 as shown in FIG. 19A. Needle assembly 540 comprises housing 516 together with a needle cannula 512 mounted therein on hub 518, the hub 518 being disposed in chamber 516a (FIG. 18B). Needle assembly 540 also comprises a blunting member comprising a blunting probe 528 carried on a shuttle 530. Shuttle 530 carries a lug 534 on a resilient arm portion 534a. Shuttle 530 also comprises a plunger portion 530a on which the blunting probe 528 is mounted. Plunger portion 530a is dimensioned and configured for a close fit with aperture 518a (FIG. 18C) and a seal is achieved therewith by means of a bushing 554, which is held in place by the wall around aperture 518a and the rearward end of needle hub 518. Needle cannula 512 and blunting probe 528 are dimensioned and configured so that the blunting probe 528 can be telescopically received within needle cannula 512, optionally but preferably without preventing fluid flow therethrough.

To assemble needle assembly 540, bushing 554 is disposed in chamber 516a, and then the needle hub 518, with needle cannula 512 thereon, is inserted into chamber 516a. Cap 517 is then secured in place. The blunting member is inserted from the rearward end of housing 516 so that blunting probe 528 enters aperture 518a, passes through chamber 516a and telescopically enters needle cannula 512. Shuttle 530 is dimensioned and configured to permit sufficient forward and rearward movement so that blunting probe 528 can be moved forward to a blunting configuration where the blunt tip thereof extends beyond the sharp tip of the needle and thus blunts the device, to a withdrawn position in which the blunt end of blunting probe 528 is withdrawn into the needle, thus rendering the device sharp.

Figure 20:
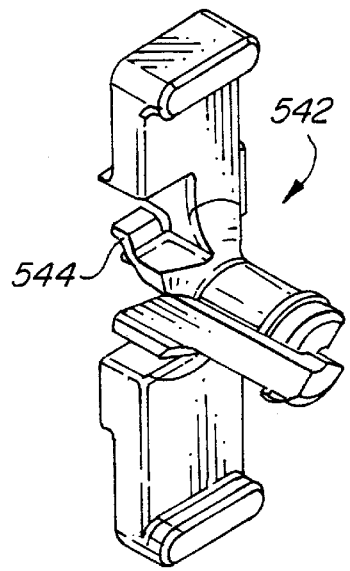
FIG. 20 is a perspective view of an accessory device for use with the needle assembly of FIGS. 19A and 19B.

Arm 534a and lug 534 are dimensioned and configured so that when the blunting member is in the forward, blunting position, lug 534 engages stay 522. An accessory device 542 can be installed on the device to disengage lug 534 from stay 522 and push the blunting member rearward in the housing to the position shown in FIG. 19B, thus sharpening the device. In a particular embodiment, accessory 542 defines a pawl 544 which engages lug 534 on shuttle 530. As suggested in FIG. 20 by the generally symmetrical configuration with a narrow center region, accessory 542 may optionally be capable of being manually split apart. Thus, accessory 542 is fissile and may carry a fissile device such as a peelable catheter. Optionally, after the needle assembly is withdrawn, the catheter or accessory 542 may be used as an introducer for another device from which it may be removed by being pulled apart.

While the invention has been described in detail with reference to particular embodiments thereof, it will be apparent upon a reading and understanding of the foregoing, that numerous alterations and variations to the described embodiments may occur to those skilled in the art, and that such alterations and variations will lie within the scope of the appended claims.

What is claimed is:

1. A needle assembly comprising:
   a needle member comprising a needle cannula mounted in a housing, the needle cannula comprising a puncture tip and comprising a needle passageway extending substantially lengthwise through the needle cannula;
   a blunting member comprising a blunting probe, the blunting probe comprising a blunt end, the blunting probe being disposed telescopically within the needle cannula while permitting flow through the needle passageway, the needle assembly being movable between a sharpened configuration in which the puncture tip of the needle cannula is exposed and a blunted configuration in which the blunt end of the blunting probe blunts the needle assembly; and
   releasable locking means for releasably locking the needle assembly in the blunted configuration, the releasable locking means comprises a movable detent and a stay against which the detent may bear when the needle assembly is in the blunted configuration, the detent being movable between a locking position in which it prevents the needle assembly from moving to the sharpened configuration and an unlocked position which permits the needle assembly to move to the sharpened configuration.

2. The needle assembly of claim 1, wherein the housing defines a chamber in fluid communication with the passageway of the needle cannula, and wherein the releasable locking means is located inside the chamber.

3. The needle assembly of claim 1, wherein the housing defines a chamber in fluid communication with the passageway of the needle cannula, and wherein the releasable locking means is located outside the chamber.

4. The needle assembly of claim 3, wherein the housing further defines an open channel within which the releasable locking means is disposed.

5. A needle assembly comprising:
   a needle member comprising a needle cannula mounted in a housing, the needle cannula comprising a puncture tip and comprising a needle passageway extending substantially lengthwise through the needle cannula, the housing defining a chamber in fluid communication with the passageway of the needle cannula, the housing further defining an open channel comprising a stay;
   a blunting member comprising a blunting probe mounted in a shuttle, the blunting probe comprising a blunt end and being disposed telescopically within the needle cannula while permitting flow through the needle passageway, the blunting probe being movable between a sharpened configuration in which the puncture tip of the needle cannula is exposed and a blunted configuration in which the blunt end of the blunting probe blunts the needle assembly;
   wherein one of the shuttle and housing comprises a movable detent, and the other comprises a stay, the detent being movable between a locking position in which it may bear against the stay and prevent the needle assembly from moving to the sharpened configuration and an unlocked position which permits the needle assembly to move to the sharpened configuration.

6. A needle assembly according to claim 5, wherein the shuttle comprises the movable detent.

7. A needle assembly according to claim 7, wherein the detent extends outside the housing.

8. A needle assembly according to claim 5 or claim 6, wherein the detent further comprises a coupling site.

9. A needle assembly comprising:
   a needle member comprising a needle cannula mounted in a housing, the needle cannula comprising a puncture tip and comprising a needle passageway extending substantially lengthwise through the needle cannula, the housing defining a chamber in fluid communication with the passageway of the needle cannula, the housing further defining a stay outside the chamber;
   a blunting member comprising a blunting probe mounted in a shuttle, the shuttle carrying a movable detent, the blunting probe comprising a blunt end, the blunting probe being disposed telescopically within the needle cannula while permitting flow through the needle passageway, and being movable between a sharpened configuration in which the puncture tip of the needle cannula is exposed and a blunted configuration in which the blunt end of the blunting probe blunts the needle assembly;
   wherein the detent is movable between a locking position in which it may bear against the stay and prevent the needle assembly from moving to the sharpened configuration and an unlocked position which permits the needle assembly to move to the sharpened configuration; and the movable detent comprising a coupling site for engagement by an accessory.

10. A needle assembly according to claim 9, wherein the housing further defines an open channel and further wherein the stay is disposed within the open channel.

11. An accessory-needle apparatus comprising:
a needle member comprising a needle cannula mounted in a housing, the needle cannula comprising a puncture tip and comprising a needle passageway extending substantially lengthwise through the needle cannula, the housing defining a chamber in fluid communication with the passageway of the needle cannula, the housing further defining a stay outside the chamber;
a blunting member comprising a blunting probe, the blunting probe comprising a blunt end, the blunting probe being disposed telescopically within the needle cannula while permitting flow through the needle passageway, and being movable between a sharpened configuration in which the puncture tip of the needle cannula is exposed and a blunted configuration in which the blunt end of the blunting probe blunts the needle assembly, the blunting member also comprising a shuttle carrying a movable detent which may bear against the stay when the needle assembly is in the blunted configuration, the detent being movable between a locking position in which it prevents the needle assembly from moving to the sharpened configuration and an unlocked position which permits the accessory-needle apparatus to move to the sharpened configuration; and
an accessory dimensioned and configured to engage and move the detent to the unlocked position when the accessory engages the needle member.

12. The accessory-needle apparatus of claim 11, wherein the accessory is selected from the group consisting of a catheter, a Y-line adapter and a medication vial.

13. The accessory-needle apparatus of claim 11, wherein the detent further comprises:
an oblique flange, dimensioned and configured such that when the coupling site engages the accessory, the detent moves to the unlocked position.

14. A blood collection needle comprising:
a holder dimensioned and configured to receive therein at least one end of a blood collection tube;
a safety needle assembly comprising a needle cannula mounted in a housing, the needle cannula comprising a puncture tip and a needle passageway extending substantially lengthwise through the needle cannula, the safety needle assembly further comprising a blunting member, the blunting member comprising a blunting probe and a shuttle on which the probe is mounted, the probe having a blunt end and a blood collection end and a blunting member passageway extending from the blunt end to the collection end;
the blunting probe being disposed telescopically within the needle cannula while permitting fluid communication from the needle passageway to the blunting member passageway, and being movable between a sharpened configuration in which the puncture tip of the needle cannula is exposed and a blunted configuration in which the blunt tip of the blunting probe blunts the blood collection needle;
wherein the needle housing and the shuttle are dimensioned and configured for releasably locking the needle assembly in at least one of the blunted configuration and the sharpened configuration, and further wherein the safety needle assembly is disposed within the holder, with the puncture tip protruding therefrom, wherein the holder further comprises means for moving the blunting probe between the sharpened configuration and the blunted configuration;
wherein the means for moving comprises:
a longitudinal slot in the holder and first and second locking regions extending therefrom; and
a transmitting sleeve slidably disposed within the holder, the sleeve comprising a tab protruding from the holder through one of the slot and the first and second locking regions, the sleeve further comprising a swiping ring dimensioned and configured to unlock the safety needle assembly when the tab is moved from a locking region to the slot, and to lock the safety needle assembly when the tab is moved from the slot to a locking region.

15. A needle assembly comprising:
a needle member comprising a needle cannula mounted in a housing, the needle cannula comprising a puncture tip and comprising a needle passageway extending substantially lengthwise through the needle cannula;
a blunting member comprising a blunting probe mounted in a shuttle wherein the shuttle is disposed in the housing, the shuttle comprising a body and a movable detent, the detent comprising a base, the body and the base each having an aperture therein, a base aperture having an outlet and a body aperture having a guide surface that is offset from but converges to the body aperture, the blunting probe being disposed telescopically within the needle cannula while permitting flow through the needle passageway, and being movable between a sharpened configuration in which the puncture tip of the needle cannula is exposed and a blunted configuration in which a blunt end of the blunting probe blunts the needle assembly;
wherein the housing defines a first shoulder thereon and the shuttle is dimensioned and configured so that the detent can engage the first shoulder when the apparatus is in the blunted configuration and the detent is in the locking position;
wherein the detent is movable between a locking configuration in which the base aperture outlet is aligned with the guide surface and a released configuration in which the base aperture outlet is aligned with the body aperture.

16. The needle assembly of claim 15, wherein the housing defines a groove providing a second shoulder against which the detent may bear when the arm is in the locking position and the needle assembly is in the sharpened configuration.

17. A needle assembly comprising:
a blunting member comprising a blunting probe mounted in a blunting member hub, wherein the probe has a blunt end and a blood collection end and a blunting member passageway extending from the blunt end to the collection end, the blunting member further comprising an interior;
a needle member comprising a needle cannula, the needle cannula having a puncture tip and with a needle passageway extending substantially lengthwise through the cannula, and the needle member further comprising a needle shuttle on which the cannula is mounted, the needle shuttle being disposed telescopically within the blunting member interior;
the blunting probe being disposed telescopically within the needle cannula;

wherein the needle shuttle is movable between a releasably locked sharpened configuration in which the puncture tip of the needle cannula is exposed and a releasably locked blunted configuration in which the blunt end of the blunting probe blunts the needle assembly.

18. The needle assembly of claim 1 wherein the housing defines a contact surface for resting against a patient's skin and wherein the releasable locking means is obliquely offset from the needle cannula relative to the contact surface.

19. The needle assembly of claim 18 wherein the releasable locking means is beside the needle cannula relative to the contact surface.

20. The accessory-needle apparatus of claim 11 wherein the housing defines a contact surface for resting against a patient's skin and wherein the stay and the movable detent are obliquely offset from the needle cannula relative to the contact surface.

21. The needle assembly of claim 5, claim 9 or claim 15 wherein the housing defines a contact surface for resting against a patient's skin and wherein the stay and the movable detent are obliquely offset from the needle cannula relative to the contact surface.

* * * * *